(12) United States Patent
Brenner et al.

(10) Patent No.: US 6,277,872 B1
(45) Date of Patent: Aug. 21, 2001

(54) OXADIAZOLES, PROCESSES FOR THEIR PREPARATION AND THEIR USE AS MEDICAMENTS

(75) Inventors: Michael Brenner, Bingen am Rhein; Roland Maier, Biberach an der Riss; Marion Wienrich, Weiterstadt; Thomas Weiser, Nieder-Olm; Rainer Palluk, Bingen am Rhein; Wolf-Dietrich Bechtel, Appenheim, all of (DE); Angelo Sagrada, Milan (IT); Helmut Ensinger, Ingelheim am Rhein; Uwe Pschorn, Mainz, both of (DE); Raffaele Cesana, Milan (IT)

(73) Assignee: Boehringer Ingelheim KG, Ingelheim (DE)

( * ) Notice: Subject to any disclaimer, the term of this patent is extended or adjusted under 35 U.S.C. 154(b) by 0 days.

(21) Appl. No.: 09/284,382

(22) PCT Filed: Oct. 15, 1997

(86) PCT No.: PCT/EP97/05693

§ 371 Date: Jul. 26, 1999

§ 102(e) Date: Jul. 26, 1999

(87) PCT Pub. No.: WO98/17652

PCT Pub. Date: Apr. 30, 1998

(30) Foreign Application Priority Data

Oct. 18, 1996 (DE) .............................. 196 43 037

(51) Int. Cl.⁷ .......................... C07D 271/06; A61K 31/41
(52) U.S. Cl. .......................... 514/364; 544/138; 544/367; 546/277; 548/131
(58) Field of Search ............................ 548/131; 544/138, 544/367; 546/277; 514/364

(56) References Cited

U.S. PATENT DOCUMENTS 5,330,990 * 7/1994 Hansen ................................. 514/299

* cited by examiner

*Primary Examiner*—Robert Gerstl
(74) *Attorney, Agent, or Firm*—Robert P. Raymond; Alan R. Stempel; Mary-Ellen M. Devlin

(57) ABSTRACT

The invention relates to oxadiazole derivatives of general formula (I)

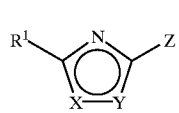

(I)

wherein X, Y, Z and $R^1$ are defined as described in the specification and claims, processes for preparing them and their use as pharmaceutical compositions.

8 Claims, No Drawings

OXADIAZOLES, PROCESSES FOR THEIR PREPARATION AND THEIR USE AS MEDICAMENTS

The invention relates to new oxadiazole derivatives, processes for preparing them and their use as pharmaceutical compositions.

The new oxadiazole derivatives have the structure of general formula (I)

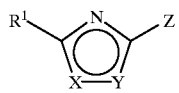
(I)

wherein

X and Y denote oxygen or nitrogen, but X and Y do not both simultaneously denote oxygen or nitrogen;

Z denotes a group of formula

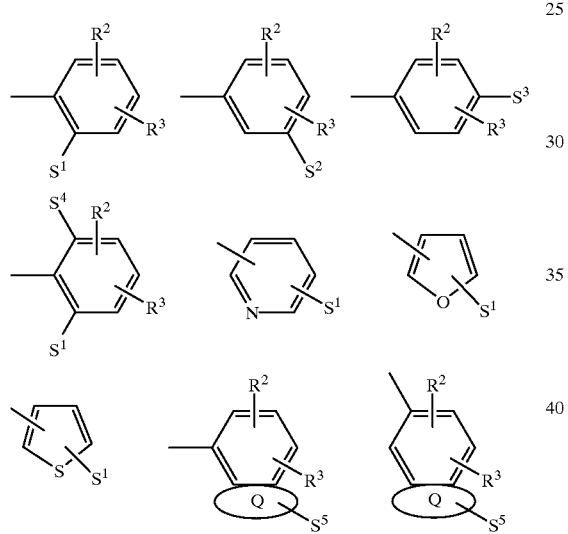

wherein $S^1$ and $S^2$ denote a group of formula

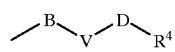

wherein V denotes oxygen, sulphur or $NR^7$ and B and D, which may be identical or different, may represent a $C_{1-10}$-alkylene, $C_{2-10}$-alkenylene or $C_{2-10}$-alkynylene bridge, which may in each case be mono- or polysubstituted by =O, —CN, —CHO, $C_{6-10}$-aryl, $COOR^7$, —$CONHSO_2R^7$, —$CONR^5R^6$, —CH=$NOR^7$, —$COR^8$, —CH($OR^7$)$R^8$, —CH($OR^7$)$_2$, —CH=CH—$R^9$, —$NR^5R^6$, —$NHCOR^7$, —$NHCONR^5R^6$, —$NHCOOR^7$, —$OR^7$, —$OCOR^7$, —$OCOOR^7$, —$OCONR^5R^6$, —$SR^7$, —$SOR^7$, —$SO_2R^7$, —$SO_3H$, —$SO_2NR^5R^6$, halogen, 1,3-dioxolane or 1,3-dioxane;

$S^1$ and $S^2$ denote a group of formula

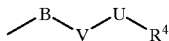

wherein V and B may have the meanings given hereinbefore and U represents a $C_{3-6}$-cycloalkyl, $C_{5-6}$-cycloalkyl or $C_{6-10}$-aryl group, which may be mono- or polysubstituted by $C_{1-4}$-alkyl, —CN, —CHO, —$COR^8$, —$NR^5R^6$, —$OR^7$, —$SR^7$, —$SO_2R^7$, —$SOR^7$ or halogen, $S^1$ and $S^2$ denote a group of formula

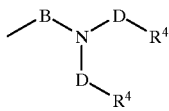

wherein B and D are as hereinbefore defined and the two groups D and the two groups $R^4$ are identical or different, $S^1$ and $S^2$ denote a group of formula

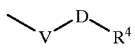

whilst V and D are as hereinbefore defined, $S^1$ and $S^2$ denote a group of formula

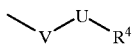

wherein V and U are as hereinbefore defined, $S^1$ and $S^2$ denote a group of formula

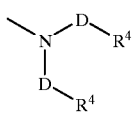

wherein D is as hereinbefore defined and the two groups D and the two groups $R^4$ are identical or different, $S^1$ and $S^2$ denote a group of formula

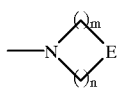

wherein E denotes oxygen, sulphur or $NR^7$ (with n,m=1,2 or 3 and n+m>2), wherein the group is optionally substituted by halogen, =O, $OR^7$, —$OCOR^7$ or one or more $C_1$–$C_6$-alkyl-, $C_{2-6}$alkenyl or $C_{2-6}$-alkynyl groups;

$S^1$ and $S^2$ denote a group of formula

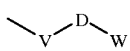

wherein V and D are as hereinbefore defined and W may be a group of the formula

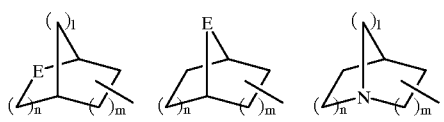

optionally substituted by halogen, =O, —OR$^7$, —OCOR$^7$, C$_{1-4}$-alkyl, C$_{2-6}$-alkenyl or C$_{2-6}$-alkynyl, wherein E denotes oxygen, sulphur or NR$^7$ and n, m, l may be 0, 1 or 2, or W is a C-linked 5, 6 or 7-membered heterocyclic group which contains one or more heteroatoms from the group comprising nitrogen, oxygen or sulphur and may optionally be substituted by benzoyl or C$_{1-4}$-alkyl;

S$^1$ and S$^2$ denote a group of formula

wherein V and W are as hereinbefore defined;
S$^1$ and S$^2$ denote a group of formula

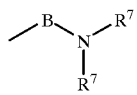

wherein B is as hereinbefore defined and the two groups R$^7$ may be identical or different,
S$^1$ and S$^2$ denote a group of formula

wherein the two groups R$^7$ may be identical or different,
S$^3$ and S$^4$ denote a group of formula

wherein B, V and D are as hereinbefore defined,
S$^3$ and S$^4$ denote a group of formula

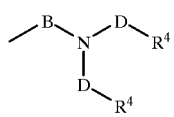

wherein B and D are as hereinbefore defined and the two groups D and the two groups R$^4$ may be identical or different,
S$^3$ and S$^4$ denote a group of formula

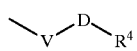

whilst V and D are as hereinbefore defined,

S$^3$ and S$^4$ denote a group of formula

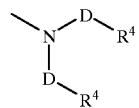

wherein D is as hereinbefore defined and the two groups D and the two groups R$^4$ are identical or different, Q denotes a fused-on, mono- or polyunsaturated 5-, 6- or 7-membered ring which may contain one or more heteroatoms from the group comprising oxygen, nitrogen or sulphur, and may optionally be substituted by OR$^7$, NR$^5$R$^6$, halogen, CN, nitro, CF$_3$, COOR$^7$, C$_{1-10}$-alkyl, C$_{2-10}$-alkenyl or C$_{2-10}$-alkynyl;

S$^5$ denotes a group of formula

wherein D is as hereinbefore defined;

R$^1$ denotes hydrogen, a C$_{1-10}$-alkyl-, C$_{2-10}$-alkenyl or C$_{2-10}$-alkynyl group, which may optionally be mono- or polysubstituted by —CN, —CHO, —COOR$^7$, —CONHSO$_2$R$^7$, —CONR$^5$R$^6$, —CH=NOR$^7$, —COR$^8$, —CH(OR$^7$)R$^8$, —CH(OR$^7$)$_2$, —CH=CH—R$^9$, —NR$^5$R$^6$, —NHCOR$^7$, —NHCONR$^5$R$^6$, —NHCOOR$^7$, =O, —OR$^7$, —OCOR$^7$, —OCOOR$^7$, —OCONR$^5$R$^6$, —SR$^7$, —SOR$^7$, —SO$_2$R$^7$, —SO$_3$H, —SO$_2$NR$^5$R$^6$, halogen, 1,3-dioxolane or 1,3-dioxane, R$^1$ denotes phenyl, which may optionally be mono-, di- or trisubstituted directly or via a C$_{1-4}$-alkylene bridge by one or more of the following groups: halogen, C$_1$–C$_4$-alkyl, —CF$_3$, —CHO, —COOR$^7$, —CONR$^5$R$^6$, —CONHSO$_2$R$^7$, —CR$^7$=NOR$^7$ (wherein the groups R$^7$ may be identical or different), —COR$^8$, —CH(OH)R$^8$, —CH(OR$^7$)$_2$, —CH=CH—R$^9$, —NR$^5$R$^6$, —NO$_2$, —C$_1$–C$_4$-alkyl-NR$^5$R$^6$, —NHCOR$^7$, —NHCOOR$^7$, —NHCONR$^5$R$^6$, —NH—SO$_2$R$^7$, —OR$^7$, —OCOR$^7$, OCONR$^5$R$^6$, —SR$^7$, —SOR$^7$, —SO$_2$R$^7$, —SO$_3$H, —SO$_2$NR$^5$R$^6$ or by a group of formula

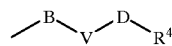

wherein B, V and D are as hereinbefore defined,
R$^1$ denotes phenyl, which may be substituted by a group of formula

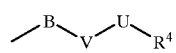

wherein B, V and U are as hereinbefore defined,
R$^1$ denotes phenyl, which is substituted by a group of formula

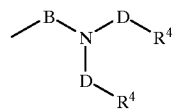

wherein B and D are as hereinbefore defined and the two groups D and the two groups R$^4$ are identical or different, R$^1$ denotes phenyl, which is substituted by a group of formula

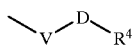

wherein V and D are as hereinbefore defined,
R¹ denotes phenyl, which is substituted by a group of formula

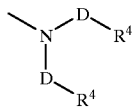

wherein D is as hereinbefore defined and the two groups D and the two groups R⁴ are identical or different,
R¹ denotes phenyl, which is substituted by a group of formula

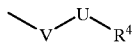

wherein V and U are as hereinbefore defined,
R¹ denotes phenyl, which is substituted by a group of formula

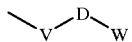

wherein V, D and W are as hereinbefore defined;
R¹ denotes phenyl, which is substituted by a group of formula

wherein V and W are as hereinbefore defined;
R¹ denotes phenyl-$C_{1-6}$-alkyl, preferably phenyl-$C_{1-4}$-alkyl, phenyl-$C_{2-6}$-alkenyl or phenyl-$C_{2-6}$-alkynyl, wherein the phenyl ring may optionally be substituted either directly or via an alkylene bridge having 1 to 4 carbon atoms by one or more, preferably one of the groups: halogen, $C_{1-4}$-alkyl, —$CF_3$, —CHO, —$COOR^7$, —$CONR^5R^6$, —$CONHSO_2R^7$, —$CR^7=NOR^7$ (wherein the groups $R^7$ may be identical or different), —$COR^8$, —CH(OH)$R^8$, —CH(OR$^7$)$_2$, —CH=CH—$R^9$, —$NR^5R^6$, —$NO_2$, —$C_{1-4}$-alkyl—$NR^5R^6$, —$NHCOR^7$, —$NHCOOR^7$, —$NHCONR^5R^6$, —NH—$SO_2$—$R^7$, —$OR^7$, —$OCOR^7$, —$OCONR^5R^6$, —$SR^7$, —$SOR^7$, —$SO_2R^7$, —$SO_3H$ or —$SO_2NR^5R^6$,
R¹ denotes $C_{3-7}$-cycloalkyl-$C_{1-6}$-alkyl, $C_{3-7}$-cycloalkyl-$C_{2-6}$-alkenyl, $C_{3-7}$-cycloalkyl-$C_{2-6}$-alkynyl, wherein the cycloalkyl group is optionally substituted, either directly or via an alkylene bridge having 1 to 4 carbon atoms, by one or more—preferably one—of the groups —CN, —CHO, —$COOR^7$, —$CONHSO_2R^7$, —$CONR^5R^6$, —CH=$NOR^7$, —$COR^8$, —CH(OR$^7$)$R^8$, —CH(OR$^7$)$_2$, —CH=CH—$R^9$, —$NR^5R^6$, —$NHCOR^7$, —$NHCONR^5R^6$, —$NHCOOR^7$, =O, —$OR^7$, —$OCOR^7$, —$OCOOR^7$, —$OCONR^5R^6$, —$SR^7$, —$SOR^7$, —$SO_2R^7$, —$SO_3H$, —$SO_2NR^5R^6$, halogen, 1,3-dioxolane or 1,3-dioxane,
R¹ denotes a group of formula M, M-$C_{1-6}$-alkyl, M-CONH—$C_{1-6}$-alkyl, M-CONH—$C_{2-6}$-alkenyl, M-CONH—$C_{2-6}$-alkynyl, M-NH—CO—$C_{1-6}$-alkyl, M-NH—CO—$C_{1-6}$-alkenyl, M-NH—CO—$C_{1-6}$-alkynyl, M-$C_{2-6}$-alkenylene or M-$C_{2-6}$-alkynylene, wherein M is a C- or N-linked 5, 6 or 7-membered heterocycle which contains one or more heteroatoms from the group comprising nitrogen, oxygen or sulphur and may optionally be mono- or polysubstituted, preferably monosubstituted by phenyl, substituted phenyl, benzyl, substituted benzyl, $C_{1-4}$-alkyl, halogen, —$OR^7$, —CN, —$NO_2$, —$NH_2$, —$CH_2NR^5R^6$, —OH, =O, a ketal, ethyleneketal, —COOH, $SO_3H$, —$COOR^7$, —$CONR^5R^6$, —$COR^8$, —$SO_2$—$R^7$ or —$CONR^5R^6$,
R¹ denotes $C_3$–$C_7$-cycloalkyl, which is optionally substituted by —CN, —CHO, —$COOR^7$, —$CONHSO_2R^7$, —$CONR^5R^6$, —CH=$NOR^7$, —$COR^8$, —CH(OR$^7$)$R^8$, —CH(OR$^7$)$_2$, —CH=CH—$R^9$, —$NR^5R^6$, —$NHCOR^7$, —$NHCONR^5R^6$, —$NHCOOR^7$, =O, —$OR^7$, —$OCOR^7$, —$OCOOR^7$, —$OCONR^5R^6$, —$SR^7$, —$SO_2R^7$, —$SOR^7$, —$SO_2R^7$, —$SO_3H$, —$SO_2NR^5R^6$, halogen, 1,3-dioxolane or 1,3-dioxane,
R¹ denotes a norbornene or norbornene group optionally substituted by $C_{1-4}$-alkyl, preferably methyl, a $C_{3-6}$-dicycloalkyl-methyl, preferably dicyclopropylmethyl, adamantane or noradamantane group,
R¹ denotes an optionally substituted group of formula

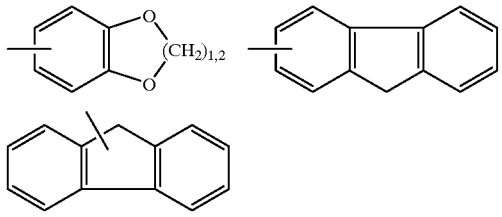

R¹ denotes an optionally substituted group of formula

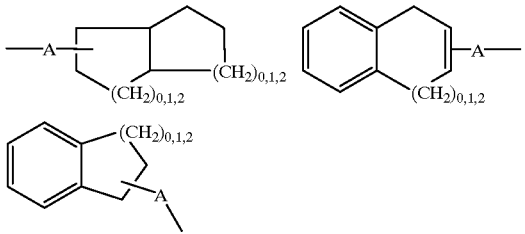

wherein A is a single bond or an alkylene, an alkenylene or an alkynylene group having up to 6, preferably up to 4 carbon atoms in the chain,
R¹ denotes a [3,3,0]-bicyclo-octane, preferably a [3,3,0]-bicyclo-octan-2-yl;
R² and R³ which may be identical or different denote hydrogen, mercapto, $NR^5R^6$, halogen, nitro, $CF_3$, —$OR^7$, —$SR^7$, $COOR^7$, a $C_{1-10}$-alkyl, $C_{2-10}$-alkenyl or $C_{2-10}$-alkynyl group, which is optionally substituted by —CN, —CHO, —$COOR^7$, —$CONHSO_2R^7$, —$CONR^5R^6$, —CH=$NOR^7$, —$COR^8$, —CH(OR$^7$)$R^8$, —CH(OR$^7$)$_2$, —CH=CH—$R^9$, —$NR^5R^6$, —$NHCOR^7$, —$NHCONR^5R^6$, —$NHCOOR^7$, =O, —$OR^7$, —$OCOR^7$, —$OCOOR^7$, —$OCONR^5R^6$, —$SR^7$, —$SOR^7$, —$SO_2R^7$, —$SO_3H$, —$SO_2NR^5R^6$, halogen, 1,3-dioxolane or 1,3-dioxane or
R² and R³ denote $C_{6-10}$-aryl, preferably phenyl, aryl-$C_{1-6}$-alkyl, preferably benzyl, $C_{6-10}$-aryloxy, preferably phenyloxy, $R^2$ and $R^3$ together denote a group of general formula

wherein G represents a fused, mono- or poly- preferably polyunsaturated 5, 6 or 7-membered ring, which may contain one or more heteroatoms from the group comprising oxygen, nitrogen or sulphur and is optionally substituted by $OR^7$, $NR^5R^6$, halogen, CN, nitro, $CF_3$, $COOR^7$, $C_{1-10}$-alkyl, $C_{2-10}$-alkenyl or $C_{2-10}$-alkynyl;

$R^4$ denotes hydroxy, halogen, nitro, $CF_3$, CN, mercapto, $C_{1-6}$-alkylmercapto, $C_{6-10}$-aryl, preferably phenyl, aryl-$C_{1-6}$-alkyl, preferably benzyl, aryl-$C_{2-6}$-alkylenyl or aryl-$C_{2-6}$-alkynyl, wherein the aromatic ring may be mono- or polysubstituted by halogen, $C_{1-4}$-alkyl, $-CF_3$, $-CHO$, $-COOR^7$, $-CONR^5R^6$, $-CONHSO_2R^7$, $-CR^7=NOR^7$ (wherein the groups R7 may be identical or different), $-COR^8$, $-CH(OH)R^8$, $-CH(OR^7)_2$, $-CH=CH-R^9$, $-NR^5R^6$, $-NO_2$, $C_{1-4}$-alkyl-$NR^5R^6$, $-NHCOR^7$, $-NHCOOR^7$, $-NHCONR^5R^6$, $-NH-SO_2-R^7$, $-OR^7$, $-OCOR^7$, $-OCONR^5R^6$, $-SR^7$, $-SOR^7$, $-SO_2R^7$, $-SO_3H$ or $-SO_2NR^5R^6$, $R^4$ denotes aryl-$C_{1-6}$-alkyloxy, preferably benzyloxy, wherein the aromatic ring may be mono- or polysubstituted by halogen, $C_{1-4}$-alkyl, $-CF_3$, $-CHO$, $-COOR^7$, $-CONR^5R^6$, $-CONHSO_2R^7$, $-CR^7=NOR^7$ (wherein the groups R7 may be identical or different), $-COR^8$, $-CH(OH)R^8$, $-CH(OR^7)_2$, $-CH=CH-R^9$, $-NR^5R^6$, $-NO_2$, $C_{1-4}$-alkyl-$NR^5R^6$, $-NHCOR^7$, $-NHCOOR^7$, $-NHCONR^5R^6$, $-NH-SO_2-R^7$, $-OR^7$, $-OCOR^7$, $-OCONR^5R^6$, $-SR^7$, $-SOR^7$, $-SO_2R^7$, $-SO_3H$ or $-SO_2NR^5R^6$, $R^4$ denotes $C_{6-10}$-aryloxy, preferably phenyloxy, wherein the aromatic ring may be mono- or polysubstituted by halogen, $C_{1-4}$-alkyl, $-CF_3$, $-CHO$, $-COOR^7$, $-CONR^5R^6$, $-CONHSO_2R^7$, $-CR^7=NOR^7$ (wherein the groups R7 may be identical or different), $-COR^8$, $-CH(OH)R^8$, $-CH(OR^7)_2$, $-CH=CH-R^9$, $-NR^5R^6$, $-NO_2$, $-C_1-C_4$-alkyl-$NR^5R^6$, $-NHCOR^7$, $-NHCOOR^7$, $-NHCONR^5R^6$, $-NH-SO_2-R^7$, $-OR^7$, $-OCOR^7$, $-OCONR^5R^6$, $-SR^7$, $-SOR^7$, $-SO_2R^7$, $-SO_3H$ or $-SO_2NR^5R^6$, $R^4$ denotes a 5-, 6- or 7-membered heterocycle, which contains as heteroatom one or more atoms from the group comprising nitrogen, oxygen or sulphur, is attached via a C-atom and is optionally mono- or polysubstituted, preferably monosubstituted, by benzyl, $C_{1-4}$-alkyl, halogen, $-OR^7$, $-CN$, $-NO_2$, $-NH_2$, $-CH_2NR^5R^6$, $-OH$, $=O$, a ketal, ethyleneketal, $-COOH$, $-SO_3H$, $-COOR^7$, $-CONR^5R^6$, $-COR^8$, $-SO_2R^7$ or $-CONR^5R^6$, $R^4$ denotes a $C_{1-10}$-alkyloxy, $C_{2-10}$-alkenyloxy or $C_{2-10}$-alkynyloxy group, which is optionally substituted by $-CN$, $-CHO$, $-COOR^7$, $-CONHSO_2R^7$, $-CONR^5R^6$, $-CH=NOR^7$, $-COR^8$, $-CH(OR^7)R^8$, $-CH(OR^7)_2$, $-CH=CH-R^9$, $-NR^5R^6$, $-NHCOR^7$, $-NHCONR^5R^6$, $-NHCOOR^7$, $=O$, $-OR^7$, $-OCOR^7$, $-OCOOR^7$, $-OCONR^5R^6$, $-SR^7$, $-SOR^7$, $-SO_2R^7$, $-SO_3H$, $-SO_2NR^5R^6$, halogen, 1,3-dioxolane or 1,3-dioxane, $R^4$ denotes $C_{3-8}$-cycloalkyloxy, preferably cyclopentyloxy or cyclohexyloxy, which is optionally substituted by $=O$, $-OR^7$ or $OCOR^7$, $R^4$ denotes an amine of formula $NR^5R^6$, $R^4$ denotes an N-oxide of formula

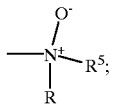

$R^5$ denotes hydrogen, $C_{3-6}$-cycloalkyl, $C_{1-10}$-alkyl, $C_{2-10}$-alkenyl or $C_{2-10}$-alkynyl which may optionally be mono- or polysubstituted by hydroxy, phenyl, which may optionally be substituted by halogen, $-OR^7$ or $C_{1-4}$-alkyl, benzyl which may optionally be substituted by halogen, $-OR^7$ or $C_{1-4}$-alkyl, $NR^7R^7$, wherein the two groups $R^7$ may be identical or different, or $C_1$-$C_8$-alkoxy, $R^5$ denotes $C_{6-10}$-aryl, preferably phenyl, which is optionally substituted by halogen, $-OR^7$, $C_{1-4}$-alkyl, preferably $-CH_3$, $-NR^7R^7$, wherein the two groups $R^7$ may be identical or different, $-SO_3H$, or $-COOR^7$;

$R^6$ denotes hydrogen, $C_{3-6}$-cycloalkyl, $C_{1-10}$-alkyl, $C_{2-10}$-alkenyl or $C_{2-10}$-alkynyl which may optionally be mono- or polysubstituted by hydroxy, phenyl, which may optionally be substituted by halogen, $-OR^7$ or $C_{1-4}$-alkyl, benzyl which may optionally be substituted by halogen, $-OR^7$ or $C_{1-4}$-alkyl, $NR^7R^7$, wherein the two groups $R^7$ may be identical or different, or $C_1$-$C_8$-alkoxy, $R^6$ denotes $C_{6-10}$-aryl, preferably phenyl, which may optionally be substituted by halogen, $-OR^7$, $C_{1-4}$-alkyl, preferably $-CH_3$, $-NR^7R^7$, wherein the two groups $R^7$ may be identical or different, $-SO_3H$, or $-COOR^7$, or $R^5$ and $R^6$ together with the nitrogen atom form a saturated or unsaturated 5- or 6-membered ring, which may contain, as further heteroatoms, nitrogen, oxygen or sulphur, wherein the heterocycle may be substituted by a branched or unbranched $C_{1-4}$-alkyl group, preferably methyl, or may carry one of the following groups: $-(CH_2)_n$-phenyl, $-(CH_2)_n-NH_2$, $-(CH_2)_n$ NH-$C_{1-4}$-alkyl, $-(CH_2)_n-N(C_1-C_8$-alkyl)$_2$, $-(CH_2)_n-NHCOOR^7$ (n=1, 2, 3, 4), halogen, $-OR^7$, $-CN$, $-NO_2$, $-NR^7R^7$, wherein the two groups $R^7$ may be identical or different, $-SO_3H$, $-COOR^7$, $CONR^7R^7$, wherein the two groups $R^7$ may be identical or different, $-SO_2-R^7$, $=O$ or a ketal-preferably $-O-CH_2-CH_2-O-$;

$R^7$ denotes hydrogen, $C_{1-4}$-alkyl, $C_{2-4}$-alkenyl, $C_{2-4}$-alkynyl, a benzyl or phenyl group, which is optionally mono- or polysubstituted by OH, chlorine, bromine or $OCH_3$;

$R^8$ denotes $C_{1-4}$-alkyl, $C_{2-4}$-alkenyl, $C_{2-4}$-alkynyl, phenyl, benzyl, $C_{3-6}$-cycloalkyl;

$R^9$ denotes $-COOR^7$, $-CH_2OR^7$, $-CONR^5R^6$, hydrogen, $C_{1-4}$-alkyl or phenyl, optionally in the form of their racemates, enantiomers, in the form of their diastereomers and mixtures thereof and optionally the pharmacologically acceptable acid addition salts thereof.

Preferred compounds of general formula (I)

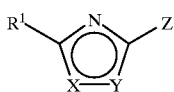

are those wherein
X and Y denote oxygen or nitrogen, wherein X and Y cannot both simultaneously be oxygen or nitrogen,
Z denotes a group of formula

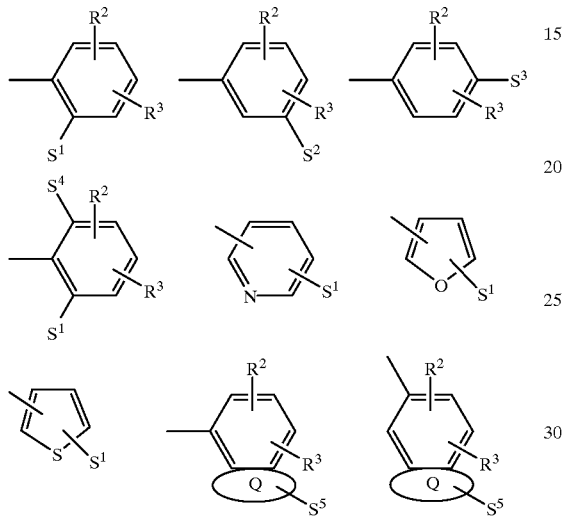

wherein
$S^1$ and $S^2$ denote a group of formula

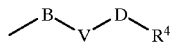

wherein V represents oxygen, sulphur or $NR^7$ and B and D, which may be identical or different, denote a $C_{1-4}$-alkylene, $C_{2-4}$-alkenylene or $C_{2-4}$-alkynylene bridge, which may be substituted by =O, —$OR^7$, —$NR^5R^6$, $C_{6-10}$-aryl or halogen, preferably fluorine, chlorine or bromine,
$S^1$ and $S^2$ denote a group of formula

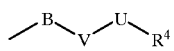

wherein V and B may have the meanings given hereinbefore and U represents a $C_{3-6}$-cycloalkyl or $C_{6-10}$-aryl group, which may be substituted by $C_{1-4}$-alkyl, —$OR^7$, —$NR^5R^6$, $C_{6-10}$-aryl or halogen, preferably fluorine, chlorine or bromine,
$S^1$ and $S^2$ denote a group of formula

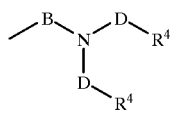

wherein B and D are as hereinbefore defined and the two groups D and the two groups $R^4$ are identical or different, $S^1$ and $S^2$ denote a group of formula

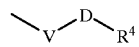

wherein V and D are as hereinbefore defined,
$S^1$ and $S^2$ denote a group of formula

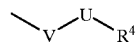

wherein V and U are as hereinbefore defined,
$S^1$ and $S^2$ denote a group of formula

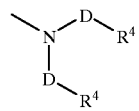

wherein D is as hereinbefore defined and the two groups D and the two groups $R^4$ are identical or different,
$S^1$ and $S^2$ denote a group of formula

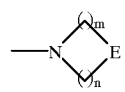

wherein E denotes oxygen, sulphur or $NR^7$ (with n,m=1,2 or 3 and n+m>2), and the group is optionally substituted by halogen, preferably fluorine, chlorine or bromine, =O, $OR^7$, or one or more $C_1$–C4-alkyl groups;
$S^1$ and $S^2$ denote a group of formula

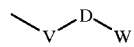

wherein V and D are as hereinbefore defined and W may be a group of the formula

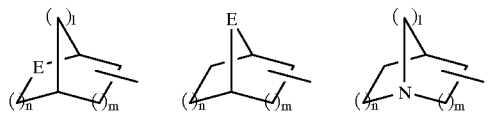

optionally substituted by halogen, =O, —$OR^7$, —$OCOR^7$, $C_{1-4}$-alkyl, $C_{2-6}$-alkenyl or $C_{2-6}$-alkynyl, wherein E denotes oxygen, sulphur or $NR^7$ and n, m, l may be 0, 1 or 2,
or W is a C-linked 5, 6 or 7-membered heterocyclic group which contains one or more heteroatoms from the group comprising nitrogen, oxygen or sulphur and may optionally be substituted by benzyl or $C_{1-14}$-alkyl;
$S^1$ and $S^2$ denote a group of formula

—V—W wherein V and W are as hereinbefore defined;

S¹ and S² denote a group of formula

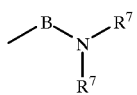

wherein B is as hereinbefore defined and the two groups R⁷ may be identical or different,
S¹ and S² denote a group of formula

wherein the two groups R⁷ may be identical or different,
S³ and S⁴ denote a group of formula

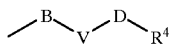

wherein B, V and D are as hereinbefore defined,
S³ and S⁴ denote a group of formula

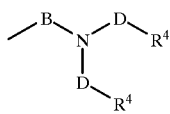

wherein B and D are as hereinbefore defined and the two groups D and the two groups R⁴ may be identical or different,
S³ and S⁴ denote a group of formula

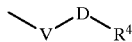

wherein V and D are as hereinbefore defined,
S³ and S⁴ denote a group of formula

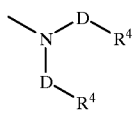

wherein D is as hereinbefore defined and the two groups D and the two groups R⁴ are identical or different,
Q denotes a fused-on, mono- or polyunsaturated 5-, 6- or 7-membered heterocyclic ring which may contain one or more heteroatoms from the group comprising oxygen, nitrogen or sulphur, and may optionally be substituted by OR⁷, NR⁵R⁶, halogen, CN, nitro, CF₃, COOR⁷, $C_{1-4}$-alkyl, $C_{2-4}$-alkenyl or $C_{2-4}$-alkynyl;
S⁵ denotes a group of formula

—D—R4 wherein D is as hereinbefore defined;
R¹ denotes hydrogen, a $C_{1-4}$-, -alkyl-, preferably methyl, $C_{2-4}$-alkenyl or $C_{2-4}$-alkynyl group, which may optionally be substituted by OR⁷, —NR⁵R⁶, halogen, preferably fluorine, chlorine or bromine or —COOR⁷, R¹ denotes phenyl, which may optionally be mono- or polysubstituted by one or more of the following groups: halogen, preferably fluorine, chlorine or bromine, $C_1$–$C_4$-alkyl, —CF₃, —CR⁷=NOR⁷ (wherein the groups R7 may be identical or different), —NR⁵R⁶, —NO₂, —OR⁷, or by a group of formula

wherein B, V and D are as hereinbefore defined,
R¹ denotes phenyl, which may be substituted by a group of formula

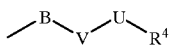

wherein B, V and U are as hereinbefore defined,
R¹ denotes phenyl, which is substituted by a group of formula

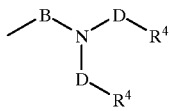

wherein B and D are as hereinbefore defined and the two groups D and the two groups R⁴ are identical or different,
R¹ denotes phenyl, which is substituted by a group of formula

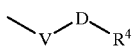

wherein V and D are as hereinbefore defined,
R¹ denotes phenyl, which is substituted by a group of formula

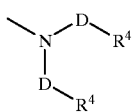

wherein D is as hereinbefore defined and the two groups D and the two groups R⁴ are identical or different,
R¹ denotes phenyl, which is substituted by a group of formula

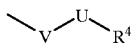

wherein V and U are as hereinbefore defined,
R¹ denotes phenyl, which is substituted by a group of formula

—V—W wherein V and W are as hereinbefore defined;
R¹ denotes phenyl, which is substituted by a group of formula

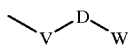

wherein V, D and W are as hereinbefore defined;

$R^1$ denotes phenyl- $C_{1-4}$-alkyl, preferably benzyl, phenyl-$C_{2-4}$-alkenyl or phenyl- $C_{2-4}$-alkynyl, wherein the phenyl ring may optionally be mono- or polysubstituted by halogen, preferably fluorine, chlorine or bromine, $C_{1-4}$-alkyl, —$CF_3$, —$CR^7$=$NOR^7$ (wherein the groups $R^7$ may be identical or different), —$NR^5R^6$, —$NO_2$ or —$OR^7$, $R^1$ denotes a group of formula M-, M- $C_{1-4}$-alkyl, M-$C_{2-4}$-alkenyl or M-$C_{2-4}$-alkynyl, wherein M is a C- or N-linked 5 or 6-membered heterocycle which contains one or more heteroatoms from the group comprising nitrogen, oxygen or sulphur and may optionally be mono- or polysubstituted, preferably monosubstituted by benzyl, $C_{1-4}$-alkyl, preferably methyl, halogen, preferably fluorine, chlorine or bromine, —$OR^7$, $NR^5R^6$ or =O, $R^1$ denotes $C_3$–$C_7$-cycloalkyl, preferably cyclopropyl or cyclopentyl, which is optionally substituted by =O or —$OR^7$, whilst the cycloalkyl group may optionally be linked via a $C_{1-4}$-alkyl bridge, $R^1$ denotes a norbornane or norbornene group optionally substituted by $C_{1-4}$-alkyl, preferably methyl, a $C_{3-6}$-dicycloalkyl-methyl, preferably dicyclopropylmethyl, adamantane or noradamantane group, $R^1$ denotes a group of formula

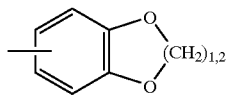

optionally mono- or polysubstituted by halogen, hydroxy or methoxy, $R^2$ and $R^3$ which may be identical or different denote hydrogen, hydroxy, amino, preferably —$NR^5R^6$, halogen, preferably fluorine, chlorine or bromine, $C_{1-4}$-alkyloxy, preferably methyloxy, $C_{1-4}$-alkyl, $R^2$ and $R^3$ together denote a group of general formula

wherein G represents a fused, mono- or poly- preferably polyunsaturated 5 or 6-membered ring, which may contain a heteroatom from the group comprising oxygen or nitrogen;

$R^4$ denotes —$OR^7$, CN or —$NR^5R^6$;

$R^4$ denotes an N-oxide of formula

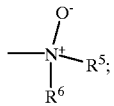

$R^5$ denotes hydrogen, $C_{3-6}$-cycloalkyl, a $C_{1-4}$-alkyl, $C_{2-4}$-alkenyl, or $C_{2-4}$-alkynyl group which may optionally be substituted by hydroxy, phenyl or $NR^7R^7$, wherein the two groups $R^7$ may be identical or different, $R^5$ denotes phenyl, which is optionally substituted by halogen, preferably fluorine, chlorine or bromine, hydroxy, methoxy, methyl or —$NR^7R^7$, wherein the two groups $R^7$ may be identical or different, $R^6$ denotes hydrogen, $C_{3-6}$-cycloalkyl, a $C_{1-4}$-alkyl, $C_{2-4}$-alkenyl, or $C_{2-4}$-alkynyl group which may optionally be substituted by hydroxy, phenyl or $NR^7R^7$, wherein the two groups $R^7$ may be identical or different, $R^6$ denotes phenyl, which may optionally be substituted by halogen, preferably fluorine, chlorine or bromine, hydroxy, methoxy, methyl or —$NR^7R^7$, wherein the two groups $R^7$ may be identical or different, or $R^5$ and $R^6$ together with the nitrogen atom form a saturated or unsaturated 5- or 6-membered ring, which may contain, as further heteroatoms, nitrogen, oxygen or sulphur, wherein the heterocycle may be substituted by a branched or unbranched $C_{1-4}$-alkyl group, preferably methyl;

$R^7$ denotes hydrogen, $C_1$–$C_4$-alkyl, $C_{2-4}$-alkenyl, $C_{2-4}$-alkynyl, a benzyl or phenyl group, which is optionally mono- or polysubstituted by OH, methoxy or halogen, preferably fluorine, chlorine or bromine;

$R^8$ denotes $C_{1-4}$-alkyl, $C_{2-4}$-alkenyl, $C_{2-4}$-alkynyl, phenyl, benzyl or $C_{3-6}$-cycloalkyl;

$R^9$ denotes —$COOR^7$, —$CH_2OR^7$, —$CONR^5R^6$, hydrogen, $C_{1-4}$-alkyl or phenyl, optionally in the form of their racemates, enantiomers, in the form of their diastereomers and mixtures thereof and optionally the pharmacologically acceptable acid addition salts thereof.

Particularly preferred are oxadiazole derivatives of general formula I

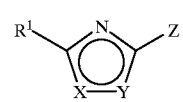

(I)

wherein

X and Y denote oxygen or nitrogen, wherein X and Y cannot both simultaneously be oxygen or nitrogen, Z denotes a group of formula

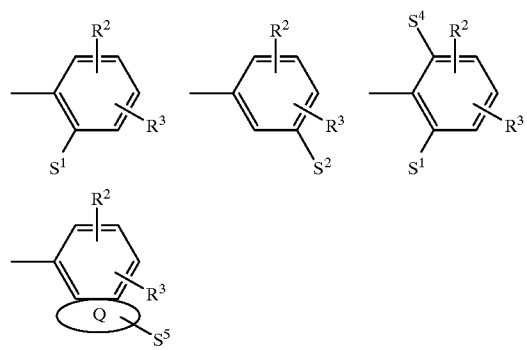

wherein $S^1$ denotes a group of formula

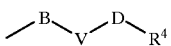

wherein V represents oxygen, sulphur or $NR^7$ and B and D, which may be identical or different, denote a $C_{1-4}$-alkylene, $C_{2-4}$-alkenylene or $C_{2-4}$-alkynylene bridge, which may be substituted by =O, —$OR^7$, phenyl or halogen, preferably fluorine, chlorine or bromine, $S^1$ denotes a group of formula

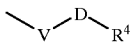

wherein V and D are as hereinbefore defined, $S^1$ denotes a group of formula

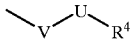

wherein V is as hereinbefore defined and U represents a $C_{3-6}$-cycloalkyl or phenyl group which may be substituted by $C_{1-4}$-alkyl, —$OR^7$, $C_{6-10}$-aryl or halogen, preferably fluorine, chlorine or bromine, $S^1$ denotes a group of formula

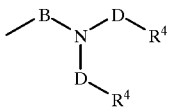

wherein B and D are as hereinbefore and the two groups D and the two groups $R^4$ are identical or different, $S^1$ denotes a group of formula

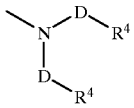

wherein D is as hereinbefore defined and the two groups D and the two groups $R^4$ are identical or different, $S^1$ denotes a group of formula

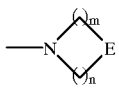

wherein E denotes oxygen, sulphur or $NR^7$ (with n,m=1,2 or 3 and n+m>2), and the group is optionally substituted by halogen, preferably fluorine, chlorine or bromine, =O, $OR^7$, or one or more $C_1$–C4-alkyl groups;

$S^1$ denotes a group of formula

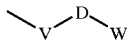

wherein V and D are as hereinbefore defined and W may be a group of the formula

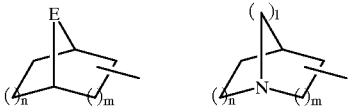

optionally substituted by halogen, =O, —O $R^7$, —OCO $R^7$, $C_{1-4}$-alkyl, $C_{2-6}$-alkenyl or $C_{2-6}$-alkynyl, wherein E denotes oxygen or $NR^7$ and n, m, l may be 0, 1 or 2, or W is a C-linked 5- or 6-membered heterocyclic group which contains one or more heteroatoms from the group comprising nitrogen, oxygen or sulphur and may optionally be substituted by benzyl or $C_{1-4}$-alkyl;

$S^1$ denotes a group of formula

—V—W wherein V and W are as hereinbefore defined;

$S^2$ denotes a group of formula

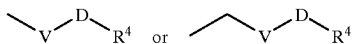

wherein V and D are as hereinbefore defined, $S^4$ denotes a group of formula

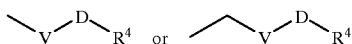

wherein V and D are as hereinbefore defined,

Q denotes a fused-on, mono- or polyunsaturated 5- or 6-membered heterocyclic ring which may contain one or more heteroatoms from the group comprising oxygen, nitrogen or sulphur, and may optionally be substituted by $OR^7$, $NR^5R^6$, halogen, CN, nitro, $CF_3$, $COOR^7$, $C_{1-4}$-alkyl, $C_{2-4}$-alkenyl or $C_{2-4}$-alkynyl;

$S^5$ denotes a group of formula

—D—$R^4$ wherein D is as hereinbefore defined;

$R^1$ denotes benzyl or phenyl, wherein the phenyl ring may optionally be mono- or polysubstituted by one or more of the following groups: fluorine, chlorine or bromine, $C_1$–$C_4$-alkyl, —$CF_3$, —$CR^7$=$NOR^7$ (wherein the groups $R^7$ may be identical or different), —$NMe_2$, $Net_2$, —$NO_2$ or —$OR^7$, $R^1$ denotes phenyl, which is substituted by a group of formula

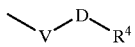

with the proviso that V is oxygen or $NR^7$ and D represents a $C_{1-4}$-alkyl bridge, $R^1$ denotes a C- or N-linked 5 or 6-membered heterocycle which contains one or more heteroatoms from the group comprising nitrogen, oxygen or sulphur and may optionally be mono- or polysubstituted by benzyl, methyl, fluorine, chlorine, bromine or hydroxy, $R^1$ denotes cyclopropyl, cyclopentyl or cyclohexyl, which is optionally substituted by =O or —$OR^7$, $R^1$ denotes norbornane, norbornene, dicyclopropylmethyl, adamantane or noradamantane, which are optionally substituted by methyl, $R^1$ denotes a group of formula

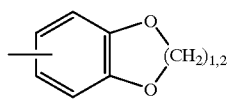

$R^1$ denotes —CH=CH-phenyl, wherein the phenyl ring may be substituted by methoxy or hydroxy, $R^2$ denotes hydrogen, fluorine, chlorine or bromine, $C_{1-4}$-alkyloxy, $C_{1-4}$-alkyl or hydroxy, $R^3$ denotes hydrogen;

$R^4$ denotes hydroxy, CN or —$NR^5R^6$;

$R^4$ denotes an N-oxide of formula

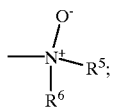

$R^5$ denotes hydrogen, $C_{1-3}$-alkyl, benzyl or phenyl;

$R^6$ denotes hydrogen, $C_{1-3}$-alkyl, benzyl or phenyl; or $R^5$ and $R^6$ together with the nitrogen atom form a saturated or unsaturated 5- or 6-membered ring, which may contain, as further heteroatoms, nitrogen, or oxygen, wherein the heterocycle may be mono- or polysubstituted by methyl;

$R^7$ denotes hydrogen, $C_1$–$C_4$-alkyl, a benzyl or phenyl group, wherein the phenyl ring is optionally mono- or polysubstituted by OH or $OCH_3$;

optionally in the form of their racemates, enantiomers, in the form of their diastereomers and mixtures thereof and optionally the pharmacologically acceptable acid addition salts thereof.

Of particular interest are compounds of general formula (I)

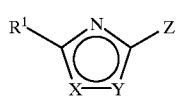

(I)

wherein

X and Y denote oxygen or nitrogen, where X and Y do not both simultaneously represent oxygen or nitrogen, Z denotes a group of formula

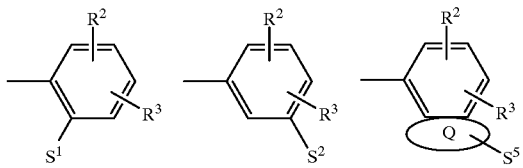

wherein $S^1$ denotes a group of formula

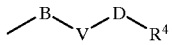

wherein V denotes oxygen, sulphur or $NR^7$, B is —CH2 and D may be one of the groups —$CH_2$, —$CH_2$—$CH_2$—, —$CH_2$—$CH_2$—$CH_2$—, —$CH_2$—$C(CH_3)H$—, —$CH_2$—CO or $CH_2$—$CH_2$—CO;

$S^1$ denotes a group of formula

wherein V and D are as hereinbefore defined, $S^1$ denotes piperazin-1-yl, 4-methyl-piperazin-1-yl or 4-benzyl-piperazin-1-yl;

$S^1$ denotes a group of formula

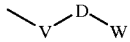

wherein V and D are as hereinbefore defined and W may represent a group of the formula

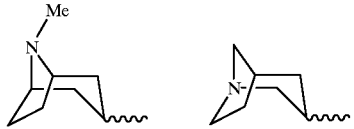

optionally substituted by $C_{1-4}$-alkyl, or W is a C-linked 5- or 6-membered nitrogen heterocycle which may optionally be substituted by benzyl or $C_{1-4}$-alkyl;

S1 denotes a group of formula

—V—W wherein V and W are as hereinbefore defined;

$S^2$ denotes a group of formula

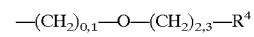

—$(CH_2)_{0,1}$—O—$(CH_2)_{2,3}$—$R^4$

Q denotes a fused-on, mono- or polyunsaturated 5- or 6-membered ring which may contain a heteroatom selected from the group comprising oxygen, nitrogen or sulphur;

S5 denotes a group of the formula

—D—$R^4$ wherein D is as hereinbefore defined;

$R^1$ denotes cyclopropyl, cyclopentyl, benzyl or phenyl, wherein the phenyl ring may be mono- or polysubstituted by one or more of the groups fluorine, chlorine, bromine, $C_{1-4}$-alkyl, —$CF_3$, —CMe=NOH, —$NO_2$ or —$OR^7$, $R^1$ denotes phenyl which is substituted by a group of formula

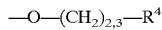

$R^1$ denotes furan, thiophene, pyridine or pyrrole, which may optionally be mono- or polysubstituted by methyl, $R^1$ denotes norbornane, norbornene, adamantane or noradamantane, $R^1$ denotes —CH=CH-phenyl, wherein the phenyl ring may be substituted by hydroxy;

$R^2$ denotes hydrogen, fluorine, chlorine, bromine, $C_{1-4}$-alkyloxy, $C_{1-4}$-alkyl or hydroxy;

R3 denotes hydrogen;

$R^4$ denotes N-morpholinyl, N-pyrrolidinyl, N-piperidinyl, N-piperazinyl, 4-methyl-piperazin-1-yl or 4-benzyl-piperazin-1-yl;

$R^4$ denotes CN, $NR^5R^6$ or an N-oxide of formula

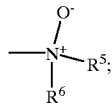

$R^5$ denotes hydrogen, $C_{1-3}$-alkyl, benzyl or phenyl;

$R^6$ denotes hydrogen, $C_{1-3}$-alkyl, benzyl or phenyl;

$R^7$ denotes hydrogen, methyl, ethyl, propyl, isopropyl, butyl, tert.-butyl, a benzyl or phenyl group, wherein the phenyl ring is optionally mono- or polysubstituted by OH or $OCH_3$, optionally in the form of their racemates, enantiomers, in the form of their diastereomers and mixtures thereof and optionally the pharmacologically acceptable acid addition salts thereof.

Also of particular interest are compounds of general formula (I)

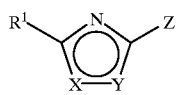

(I)

wherein

X and Y denote oxygen or nitrogen, where X and Y do not both simultaneously represent oxygen or nitrogen, Z denotes a group of formula

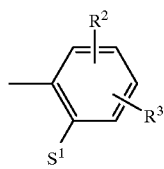 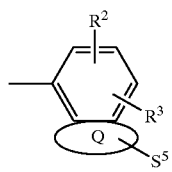

wherein $S^1$ denotes a group of formula

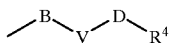

wherein V denotes oxygen, sulphur or $NR^7$, B is —$CH_2$ and D may be one of the groups —$CH_2$, —$CH_2$—$CH_2$—, —$CH_2$—$CH_2$—$CH_2$—, —$CH_2$—$C(CH_3)H$—, —$CH_2$—CO or $CH_2$—$CH_2$—CO;

$S^1$ denotes a group of formula

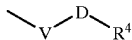

wherein V and D are as hereinbefore defined, $S^1$ denotes piperazin-1-yl, 4-methyl-piperazin-1-yl or 4-benzyl-piperazin-1-yl;

$S^1$ denotes a group of formula

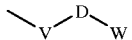

wherein V and D are as hereinbefore defined and W may represent a group of the formula

optionally substituted by $C_{1-4}$-alkyl, or W is a C-linked 5- or 6-membered nitrogen heterocycle which may optionally be substituted by benzyl or $C_{1-4}$-alkyl;

S1 denotes a group of formula

wherein V and W are as hereinbefore defined;

Q denotes a fused-on, mono- or polyunsaturated 5- or 6-membered heterocyclic ring which may contain a heteroatom selected from the group comprising oxygen, nitrogen or sulphur;

S5 denotes a group of the formula

wherein D is as hereinbefore defined;

$R^1$ denotes cyclopropyl, cyclopentyl or phenyl, wherein the phenyl ring may be mono- or polysubstituted by one or more of the groups fluorine, chlorine, bromine, $C_{1-4}$-alkyl, —$CF_3$, —CMe=NOH, —$NMe_2$, —$NO_2$ or —$OR^7$, $R^1$ denotes furan, thiophene, pyridine or pyrrole, which may optionally be mono- or polysubstituted by methyl, $R^1$ denotes norbornane, norbornene, adamantane or noradamantane, $R^1$ denotes —CH=CH-phenyl, wherein the phenyl ring may be substituted by hydroxy;

$R^2$ denotes hydrogen, fluorine, chlorine, bromine, $C_{1-4}$-alkyloxy, $C_{1-4}$-alkyl or hydroxy;

R3 denotes hydrogen;

$R^4$ denotes CN, $NR^5R^6$ or an N-oxide of formula

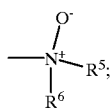

$R^4$ denotes N-morpholinyl, N-pyrrolidinyl, N-piperidinyl, N-piperazinyl, 4-methyl-piperazin-1-yl or 4-benzyl-piperazin-1-yl;
$R^5$ denotes hydrogen, $C_{1-3}$-alkyl, benzyl or phenyl;
$R^6$ denotes hydrogen, $C_{1-3}$-alkyl, benzyl or phenyl;
$R^7$ denotes hydrogen, methyl, ethyl, propyl, isopropyl, butyl, tert.-butyl, a benzyl or phenyl group, wherein the phenyl ring is optionally mono- or polysubstituted by OH or $OCH_3$, optionally in the form of their racemates, enantiomers, in the form of their diastereomers and mixtures thereof and optionally the pharmacologically acceptable acid addition salts thereof.

Also of great interest are compounds of general formula (I)

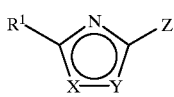

wherein
X and Y denote oxygen or nitrogen, where X and Y do not both simultaneously represent oxygen or nitrogen,
Z denotes a group of formula

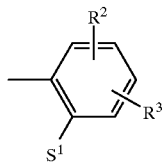 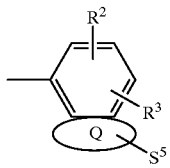

wherein
$S^1$ denotes a group of formula

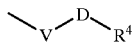

wherein V denotes oxygen, sulphur or $NR^7$ and D may be one of the groups $-CH_2-$, $-CH_2-CH_2-$, $-CH_2-CH_2-CH_2-$, $-CH_2-C(CH_3)H-$, $-CH_2-CO$ or $CH_2-CH_2-CO$;
$S^1$ denotes piperazin-1-yl, 4-methyl-piperazin-1-yl or 4-benzyl-piperazin-1-yl;
$S^1$ denotes a group of formula

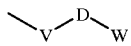

wherein V and D are as hereinbefore defined and W may represent a group of the formula

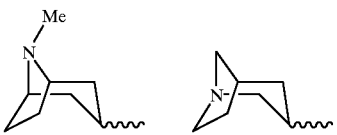

or W is a C-linked 5- or 6-membered nitrogen heterocycle which may optionally be substituted by methyl;
S1 denotes a group of formula

—V—W wherein V and W are as hereinbefore defined;
Q denotes a fused-on, mono- or polyunsaturated 5- or 6-membered heterocyclic ring which may contain a heteroatom selected from the group comprising oxygen or nitrogen;
S5 denotes a group of the formula

—D—$R^4$ wherein D is as hereinbefore defined;
$R^1$ denotes phenyl which may optionally be mono- or polysubstituted by one or more of the groups fluorine, chlorine, bromine, methyl, ethyl, n-propyl, isopropyl, n-butyl, tert. butyl, $-CF_3$ or $-OR^7$,
$R^1$ denotes furan, thiophene or pyridine, which may optionally be mono- or polysubstituted by methyl,
$R^2$ denotes hydrogen, fluorine, chlorine, bromine, methyl, methyloxy or hydroxy;
R3 denotes hydrogen;
$R^4$ denotes $NR^5R^6$ or an N-oxide of formula

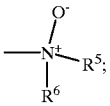

$R^4$ denotes N-morpholinyl, N-pyrrolidinyl, N-piperidinyl, N-piperazinyl, 4-methyl-piperazin-1-yl or 4-benzyl-piperazin-1-yl;
$R^5$ denotes hydrogen, methyl, ethyl, n-propyl, isopropyl, benzyl or phenyl;
$R^6$ denotes hydrogen, methyl, ethyl, n-propyl, isopropyl, benzyl or phenyl;
$R^7$ denotes hydrogen, methyl or ethyl, optionally in the form of their racemates, enantiomers, in the form of their diastereomers and mixtures thereof and optionally the pharmacologically acceptable acid addition salts thereof.

Moreover, particular importance is attached to the compounds of general formula (I)

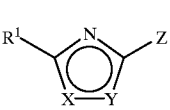

wherein
X and Y denote oxygen or nitrogen, but X and Y do not both simultaneously represent oxygen or nitrogen, Z denotes a group of formula

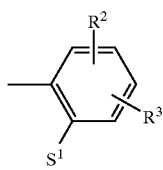 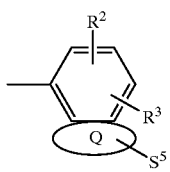

wherein
$S^1$ denotes a group of formula

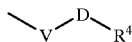

wherein V denotes oxygen and D may be one of the groups —$CH_2$—, —$CH_2$—$CH_2$—, —$CH_2$—C($CH_3$)H— or $CH_2$—$CH_2$—CO;
$S^1$ denotes N-piperazinyl or 4-benzyl-piperazin-1-yl;
$S^1$ denotes a group of formula

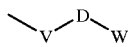

wherein V and D are as hereinbefore defined and W may represent a group of the formula

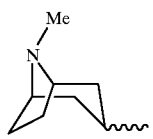 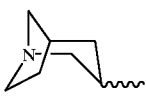

or W is a C-linked 5- or 6-membered nitrogen heterocycle which may optionally be substituted by methyl;
S1 denotes a group of formula

wherein V and W are as hereinbefore defined;
Q denotes a fused-on, mono- or polyunsaturated 5-membered heterocyclic ring which contains oxygen as heteroatom;
$S^5$ denotes a group of the formula

wherein D is as hereinbefore defined;
$R^1$ denotes phenyl which may be mono- or polysubstituted by one or more of the groups fluorine, chlorine, bromine, methyl, —$CF_3$, hydroxy, methyloxy or ethyloxy,
$R^1$ denotes furan, thiophene or pyridine;
$R^2$ denotes hydrogen, fluorine, chlorine or methyl;
R3 denotes hydrogen;
$R^4$ denotes $NR^5R^6$,
$R^4$ denotes N-morpholinyl, N-pyrrolidinyl, N-piperidinyl or 4-methyl-piperazin-1-yl;
$R^5$ denotes hydrogen, methyl, ethyl, n-propyl, isopropyl, benzyl or phenyl;
$R^6$ denotes hydrogen, methyl, ethyl, n-propyl, isopropyl, benzyl or phenyl;
optionally in the form of their racemates, enantiomers, in the form of their diastereomers and mixtures thereof and optionally the pharmacologically acceptable acid addition salts thereof.

Particularly preferred according to the invention are compounds of general formula (I)

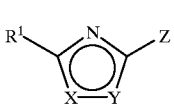

(I)

wherein
X and Y denote oxygen or nitrogen, but X and Y do not both simultaneously represent oxygen or nitrogen,
Z denotes a group of formula

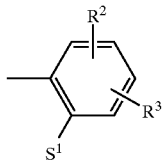 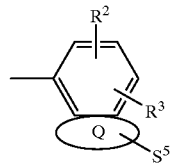

wherein
$S^1$ denotes one of the groups —O—$CH_2$—$CH_2$—$R^4$, O—$CH_2$—C($CH_3$)H—$R^4$, —O—C($CH_3$)H—$CH_2$—$R^4$ or —$CH_2$—$CH_2$—CO—$R^4$;
$S^1$ denotes 4-benzyl-piperazin-1-yl;
$S^1$ denotes one of the groups

wherein W is a C-linked 5- or 6-membered nitrogen heterocycle which may optionally be substituted by methyl;
Q denotes a fused-on, mono- or polyunsaturated 5-membered heterocyclic ring which contains oxygen as heteroatom;
$S^5$ denotes a group of the formula —$CH_2$—$R^4$;
$R^1$ denotes phenyl which may be mono- or polysubstituted by one or more of the groups fluorine, chlorine, bromine, methyl, —$CF_3$, hydroxy, methyloxy or ethyloxy,
$R^1$ denotes thiophene;
$R^2$ denotes hydrogen, fluorine, chlorine or methyl;
R3 denotes hydrogen;
$R^4$ denotes $NR^5R^6$,
$R^4$ denotes N-pyrrolidinyl or N-piperidinyl;
$R^5$ denotes hydrogen, methyl, ethyl, isopropyl, benzyl or phenyl;
$R^6$ denotes hydrogen, methyl, ethyl, isopropyl, benzyl or phenyl;
optionally in the form of their racemates, enantiomers, in the form of their diastereomers and mixtures thereof and optionally the pharmacologically acceptable acid addition salts thereof.

The term alkyl groups (including those which are components of other groups, e.g. alkylene bridges), unless otherwise stated, denotes branched and unbranched alkyl groups having 1 to 10 carbon atoms, preferably 1–4 carbon atoms. Examples include: methyl, ethyl, n-propyl, isopropyl, butyl, isobutyl, sec.butyl, tert.-butyl, pentyl, isopentyl, hexyl, heptyl and octyl. The groups methyl, ethyl, butyl or tert.-butyl are also referred to by the abbreviations Me, Et, Bu or tBu.

Unless otherwise specified, substituted alkyl groups (including those which components of other groups) may carry one or more of the following substituents, for example:

halogen, hydroxy, mercapto, $C_{1-6}$-alkyloxy, amino, alkylamino, dialkylamino, cyano, nitro, =O, —CHO, —COOH, —COO—$C_{1-6}$-alkyl, —S—$C_{1-6}$-alkyl.

Examples of alkenyl groups (including those which are part of other groups) include branched and unbranched alkenyl groups having 2 to 10 carbon atoms, preferably 2 to 3 carbon atoms, if they have at least one double bond, e.g. the alkyl groups mentioned above if they have at least one double bond, such as vinyl (provided that no unstable enamines or enol-ethers are formed), propenyl, isopropenyl, butenyl, pentenyl and hexenyl.

Unless otherwise specified, substituted alkenyl groups (including those which are part of other groups) may for example carry one or more of the following substituents: halogen, hydroxy, mercapto, $C_{1-6}$-alkyloxy, amino, alkylamino, dialkylamino, cyano, nitro, =O, —CHO, —COOH, —COO—$C_{1-6}$-alkyl, —S—$C_{1-6}$-alkyl.

Examples of alkynyl groups (including those which are part of other groups) are alkynyl groups having 2 to 10 carbon atoms provided that they have at least one triple bond, such as ethynyl, propargyl, butynyl, pentynyl and hexynyl.

Unless otherwise specified, substituted alkynyl groups (including those which are part of other groups) may, for example, carry one or more of the following substituents: halogen, hydroxy, mercapto, $C_{1-6}$-alkyloxy, amino, alkylamino, dialkylamino, cyano, nitro, =O, —CHO, —COOH, —COO—$C_{1-6}$-alkyl, —S—$C_{1-6}$-alkyl.

Examples of cycloalkyl groups having 3–6 carbon atoms include cyclopropyl, cyclobutyl, cyclopentyl or cyclohexyl, which may also be substituted by branched or unbranched $C_{1-4}$-alkyl, hydroxy and/or halogen or may be substituted as hereinbefore. The term halogen generally refers to fluorine, chlorine, bromine or iodine.

The term aryl denotes an aromatic ring system having 6 to 10 carbon atoms which, unless otherwise specified, may for example carry one or more of the following substituents: $C_{1-6}$-alkyl, $C_{1-6}$-alkyloxy, halogen, hydroxy, mercapto, amino, alkylamino, dialkylamino, $CF_3$, cyano, nitro, —CHO, —COOH, —COO—$C_{1-6}$-alkyl, —S—$C_{1-6}$-alkyl. The preferred aryl group is phenyl.

Examples of N-linked cyclic groups of general formula $NR^5R^6$ include: pyrrole, pyrroline, pyrrolidine, 2-methylpyrrolidine, 3-methylpyrrolidine, piperidine, piperazine, N-methylpiperazine, N-ethylpiperazine, N-(n-propyl)-piperazine, N-benzylpiperazine, morpholine, thiomorpholine, imidazole, imidazoline, imidazolidine, pyrazole, pyrazoline, pyrazolidine, preferably morpholine, N-benzylpiperazine, piperazine and piperidine, whilst the above-mentioned heterocycles may be substituted by $C_{1-4}$-alkyl, preferably methyl.

Examples of C-linked 5- or 6-membered heterocyclic rings which may contain nitrogen, oxygen or sulphur as heteroatoms, include furan, tetrahydrofuran, 2-methyltetrahydrofuran, 2-hydroxymethylfuran, tetrahydrofuranone, γ-butyrolactone, α-pyran, γ-pyran, dioxolane, tetrahydropyran, dioxane, thiophene, dihydrothiophene, thiolane, dithiolane, pyrrole, pyrroline, pyrrolidine, pyrazole, pyrazoline, imidazole, imidazoline, imidazolidine, triazole, tetrazole, pyridine, piperidine, pyridazine, pyrimidine, pyrazine, piperazine, triazine, tetrazine, morpholine, thiomorpholine, oxazole, isoxazole, oxazine, thiazole, isothiazole, thiadiazole, oxadiazole, pyrazolidine, whilst the heterocycle may be substituted as specified in the definitions.

"=O" denotes an oxygen atom linked via a double bond.

The present invention describes compounds which surprisingly have a high affinity for the following types of receptor: "Na⁺ channel site 2" binding site, histamine H1 receptor, 5-hydroxytryptamine 1A receptor, 5-hydroxytryptamine 2A receptor, Sigma receptor. In addition, these compounds exhibit an antagonistic activity at the AMPA receptor. The neuroprotective activity of the compounds according to the invention was also confirmed on an animal model. In the light of these findings, the compounds according to the invention may be used in neurodegenerative disorders and cerebral ischaemia of various origins.

The compounds according to the invention may be prepared using known methods, e.g. as follows.

In a first step, a nitrile of general formula (1) is reacted, following methods known from the literature (L. F. Tietze, T. Eicher, "Reaktionen und Synthesen im Organisch-chemischen Praktikum und Forschungslaboratorium", 2nd Edition, 1991, published by Georg Thieme Verlag of Stuttgart, N.Y., p. 340), with hydroxylamine to obtain an amidoxime of general formula (2) (Diagram 1). Under basic reaction conditions, the reaction of this amidoxime (2) with benzoic acid derivatives of general Formula (3) substituted by nucleophilic groups leads to oxadiazoles of general Formula (4). Benzoic acid derivatives (3) which carry functionalised side chains may be used if suitable protecting groups are used.

The base may be an alkali metal or alkaline earth metal alkoxide, e.g. of methanol, ethanol, isopropanol, n-, sec- or tert-butyl alcohol. Examples of suitable alkali metal and alkaline earth metals include lithium, sodium, potassium, magnesium and calcium. Sodium methoxide, sodium ethoxide, sodium isopropoxide, potassium-tert-butoxide and potassium ethoxide are particularly preferred as bases. In addition, alkali metal or alkaline earth metal hydrides may be used as bases according to the invention.

Diagram 1

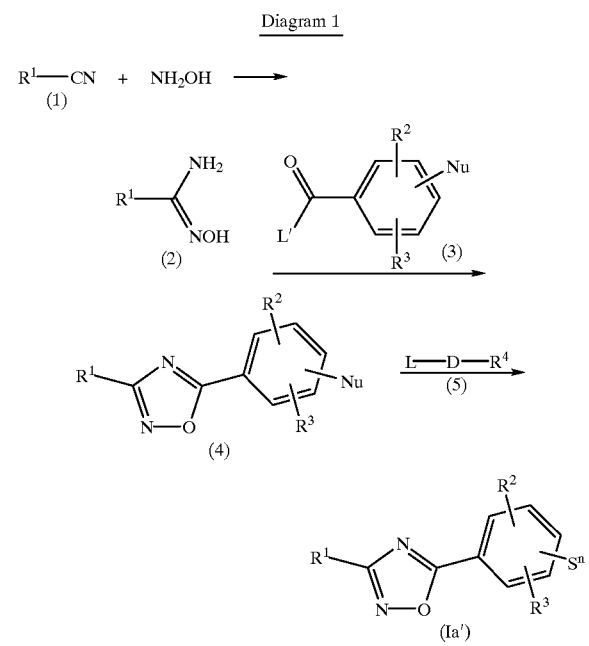

wherein
 L'=leaving group, such as chlorine, bromine or alkyloxy;
 L=leaving group, such as chlorine, bromine, iodine or methane sulphonyl;
 Nu=OH, SH, $NH_2$=VH as hereinbefore defined or Nu=—B—OH, —B—SH, —B—NH$_2$=B—VH as hereinbefore defined;

S$^n$=S$^1$, S$^2$, S$^3$, S$^4$ or S$^5$ as hereinbefore defined.

The modification of the side chain to form the oxadiazole derivatives of general formula (Ia') is carried out according to Diagram 1 by a final reaction of (4) with electrophilic compounds of general Formula (5). In order to do this, the oxadiazoles (4) are mixed with the electrophilic compounds (5) after the addition of a base in an inert solvent at ambient temperature and after a period of up to 1 hour, preferably 15 to 30 minutes, the mixture is refluxed for 4 to 12 hours, preferably 6 to 8 hours. After cooling to ambient temperature the solvent is largely distilled off in vacuo and the product is purified after washing and drying by crystallisation or chromatography. According to the invention, alkali metal or alkaline earth metal hydrides may be used as bases. The hydrides of sodium, lithium and potassium as well as magnesium and calcium are preferred. Suitable inert solvents are dimethylformamide, methylene chloride and cyclic ethers such as tetrahydrofuran or preferably dioxane. In addition, the base used may be an alkali metal or alkaline earth metal alkoxide, e.g. of methanol, ethanol, isopropanol, n-, sec- or tert-butyl alcohol. Suitable alkali and alkaline earth metals include for example lithium, sodium, potassium, magnesium, calcium, sodium methoxide, sodium ethoxide, sodium isopropoxide, potassium-tert-butoxide and potassium ethoxide. According to the invention, alkali or alkaline earth metal hydroxides of lithium, sodium and potassium as well as magnesium and calcium may also be used, but preferably sodium hydroxide, potassium hydroxide, lithium hydroxide and calcium hydroxide are used in an alcoholic or aqueous solution. Oxadiazoles of general Formula (Ia), which carry a heteroaromatic ring instead of the phenyl ring shown in (Ia'), may be prepared analogously.

According to Diagram 2, the reaction of aromatic nitriles of general Formula (6) with electrophilic compounds of general Formula (5) leads to the aromatic cyanides of general Formula (7) substituted by the side chain S$^n$ (n=1,2,3,4). For this purpose, the nitriles (6), after the addition of a base, are deprotonated in an inert solvent at ambient temperature or with heating, preferably to 40 to 80° C., and then mixed with electrophilic compounds (5). The resulting solution is heated to 40 to 80° C. for a period of 0.25 to 2 hours and after cooling to ambient temperature the solvent is eliminated in vacuo. After washing and drying, the product is used directly, without further purification, in the next step. According to the invention, alkali or alkaline earth metal hydrides, preferably hydrides of sodium, lithium, potassium, as well as magnesium and calcium may be used as bases. Suitable inert solvents are dimethylformamide, methylene chloride and cyclic ethers such as tetrahydrofuran or preferably dioxane.

Diagram 2

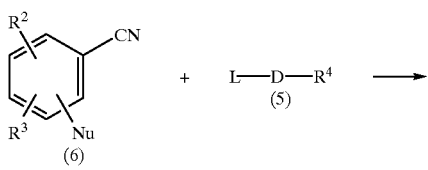

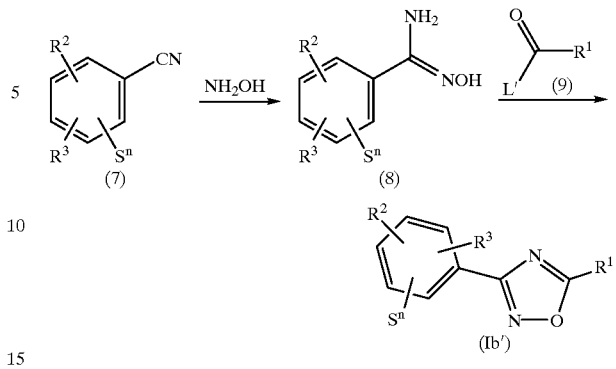

wherein

L'=leaving group, such as chlorine, bromine or alkyloxy;

L=leaving group, such as chlorine, bromine, iodine or methane sulphonyl;

Nu=OH, SH, NH$_2$=VH as hereinbefore defined or

Nu=—B—OH, —B—SH, —B—NH$_2$=B—VH as hereinbefore defined;

sn=S$^1$, S$^2$, S$^3$, S$^4$ or S$^5$ as hereinbefore defined.

These nitriles may be converted in known manner (L. F. Tietze, T. Eicher, "Reaktionen and Synthesen im Organisch-chemischen Praktikum und Forschungslaboratorium", Georg Thieme Verlag, Stuttgart, 2nd Edition, 1991, p. 340) into the aromatic amidoximes of general Formula (8). In a basic medium these amidoximes when reacted with the carboxylic acid derivatives (9) yield the oxadiazoles of formula (Ib'). For this purpose the amidoximes (8) are dissolved with the carboxylic acid derivatives (9) in an inert solvent, preferably an alcohol, most preferably ethanol, and heated with the action of a base. After cooling to ambient temperature, the solvent is largely distilled off in vacuo and after washing and drying the product is purified by crystallisation or chromatography. Suitable bases include alkali or alkaline earth metal alkoxides, e.g. of methanol, ethanol, isopropanol, n-, sec- and tert-butyl alcohol. Suitable alkali and alkaline earth metals include lithium, sodium, potassium, magnesium and calcium. Sodium methoxide, sodium ethoxide, sodium isopropoxide, potassium tert-butoxide and potassium ethoxide are particularly preferred as bases.

Oxadiazoles of general formula (Ib) which carry a heteroaromatic ring instead of the phenyl ring shown in (Ib') may be prepared analogously. Oxadiazoles of general formula (Ib) which are further functionalised in the side chain may be obtained using suitable protecting groups.

Oxadiazole derivatives of general Formula (10) which carry a side chain substituted by a leaving group at the aromatic ring may be converted according to the invention into compounds of general Formula (I') by reacting with the nucleophilic compounds of general formula (11) (Diagram 3).

Diagram 3

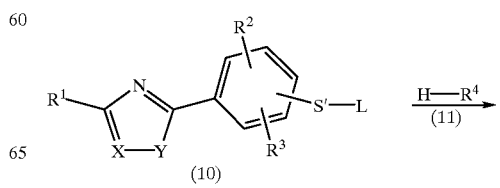

-continued

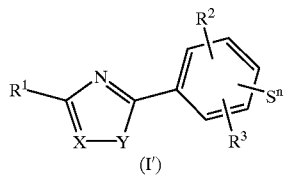

(I')

wherein
L=leaving group, such as chlorine, bromine, iodine or methane sulphonyl;
S'=—B—V—D, —V—D wherein B, V and D are as hereinbefore defined;
Sn=$S^1$, $S^2$, $S^3$, $S^4$ or S5 as hereinbefore defined.

For this purpose, the compounds (10) are dissolved in an inert solvent and, after the addition of the nucleophilic compound (11), heated to 50 to 120° C. for a period of 0.5 to 2 hours, preferably 1 to 1.5 hours. After cooling to ambient temperature the solvent is largely distilled off in vacuo and after washing and drying the product is purified by crystallisation or chromatography.

Suitable inert solvents include dimethylformamide and methylene chloride as well as cyclic ethers such as tetrahydrofuran or preferably dioxane.

Oxadiazoles of general Formula (I) which carry a heteroaromatic ring instead of the phenyl ring shown in Formula (I') may be prepared analogously. Oxadiazoles of general Formula (I) which are further functionalised in the side chains may be synthesised using suitable protecting groups.

The present invention will be illustrated by means of the following descriptions of synthesis provided by way of example.

EXAMPLE 1

5-{2-[2-(N,N-Dimethylamino)ethyl]oxymethyl-phenyl}-3-phenyl-1,2,4-oxadiazole

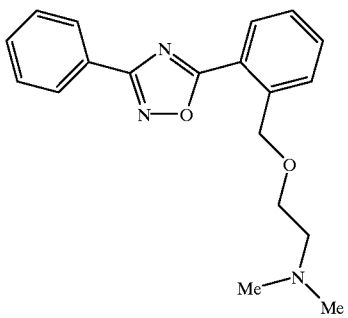

a) Preparation of the Benzoic Acid Amidoxime 14 g of hydroxylamine hydrochloride are dissolved in 50 ml water and, with stirring and cooling with ice, mixed with 16.8 g of sodium hydrogen carbonate. To this mixture is added a solution of 10.3 g of benzoic acid nitrile in 100 ml of ethanol and refluxed for 3 hours. Then the ethanol is evaporated in vacuo and the residue is extracted twice with diethylether. The combined ether phases are dried over sodium sulphate and concentrated by evaporation. The residue (13.4 g=98.5% of theory) is used in the reaction of cyclisation without further purification.

b) Preparation of 5-(2-hydroxymethyl-phenyl)-3-phenyl-1,2,4-oxadiazole 1.36 g of benzoic acid amidoxime are added to a freshly prepared solution of 0.46 g of sodium in 50 ml of anhydrous ethanol and stirred for 15 minutes. Then 2.68 g of phthalide are added with stirring and the mixture is refluxed for 15 hours. The dark red solution is evaporated down in vacuo and the residue is taken up in water. It is neutralised with 2 N hydrochloric acid and extracted with dichloromethane. The organic phase is dried over sodium sulphate, concentrated by evaporation and chromatographed with dichloromethane/methanol (98:2). Yield: 1.2 g (48% of theory).

c) Preparation of 5-{2-[2-(N,N-dimethylamino)ethyl]oxymethyl-phenyl}-3-phenyl-1 2,4-oxadiazole 1 g of 5-(2-hydroxymethyl-phenyl)-3-phenyl-1,2,4-oxadiazole is dissolved in 20 ml of DMF and combined with 0.2 g of sodium hydride (60% in oil). Then the mixture is stirred for a further 30 minutes at 20–23° C. and a mixture of 2-N,N-dimethylaminoethyl chloride and 0.22 g of sodium hydride (60% in oil) in 20 ml of DMF which has previously been stirred for 30 minutes is added. This mixture is heated to 100° C. for 5 hours, then the solvent is evaporated in vacuo. The residue is taken up in water, acidified with 2N hydrochloric acid and extracted with ethyl acetate. The aqueous phase is made alkaline with sodium hydroxide solution and extracted with dichloromethane. The organic phase is dried over sodium sulphate, evaporated down in vacuo and chromatographed on silica gel (methanol). The product is converted into the hydrochloride using ethereal HCl solution and recrystallised from ethanol/ether. Yield: 0.07 g (5% of theory), melting point 107° C. (decomposition).

EXAMPLE 2

5-{2-[2-(N,N-dimethylamino)ethyl]oxy-phenyl}-3-phenyl-1,2,4-oxadiazole

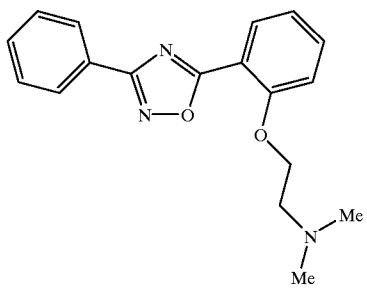

a) Preparation of 5-(2-hydroxyphenyl)-3-phenyl-1,2,4-oxadiazole 6.8 g of benzoic acid amidoxime and 15.2 g of methyl salicylate are dissolved in 150 ml of anhydrous ethanol, mixed with 2.3 g of sodium and heated 3 times for 25 minutes (with a 5 minute break each time) at 400 W in a microwave. The reaction mixture is concentrated by evaporation in vacuo to about ⅓ of its volume and the residue is mixed with water. Whilst cooling, it is adjusted to pH 8–9 with 2N hydrochloric acid, the precipitate formed is suction filtered and washed with water. In order to remove all traces of the water, the mixture is dissolved in dichloromethane, dried with sodium sulphate and concentrated by evaporation. Yield: 12.9 g (92% of theory based on benzoic acid amidoxime). m.p.: 156–158° C.

b) Preparation of 5-{2-[2-(N,N-dimethylamino)ethyl]oxy-phenyl}-3-phenyl-1,2,4-oxadiazole 2.38 g of 5-(2-hydroxyphenyl)-3-phenyl-1,2,4-oxadiazole are dissolved in 100 ml of anhydrous dioxane and stirred with 0.3 g of 80% sodium hydride suspension in oil for 15 minutes at 25–30° C. To this solution is added 60 ml of anhydrous dioxane, the resulting mixture is combined with 2.88 g of 2-(N,N-dimethylamino)ethylchloride hydrochloride and 0.6 g of 80% sodium hydride suspension in oil. This solution is also stirred for 15 minutes at 25–30° C. The combined solutions are refluxed for 8 hours, left to stand overnight and evaporated down in vacuo. The residue is mixed with water and 20 ml of 1N sodium hydroxide solution and extracted with ethyl acetate. The organic phase is dried over sodium sulphate, the solvent evaporated in vacuo and the residue chromatographed on silica gel with ethyl acetate/isopropanol (70:30, mixed with 2.5% of a 25% ammonia solution). The base thus obtained is dissolved in anhydrous ethanol, acidified with ethereal HCl and precipitated with diethyl ether. The residue is recrystallised from anhydrous ethanol and diethylether. Yield: 2.2 g (64% of theory). m.p.: 186–187° C.

EXAMPLE 3

3-{2-[2-(N,N-Dimethylamino)ethyl]oxy-phenyl}-5-phenyl-1,2,4-oxadiazole

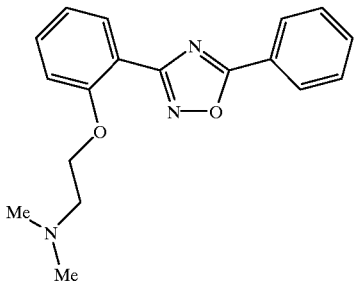

a) Preparation of 2-[2-(N,N-dimethylamino)ethyloxy]-benzoic acid nitrile 23.8 g of 2-hydroxybenzoic acid nitrile are stirred with 6.0 g of 80% sodium hydride suspension in oil in 200 ml of dioxane for 30 minutes at 60° C. To this solution are added 100 ml of anhydrous dioxane, mixed with 28.8 g of 2-(N,N-dimethylamino)ethylchloride hydrochloride and 6.0 g of 80% sodium hydride suspension in oil. This solution is also stirred for 30 minutes at 60° C. The combined solutions are heated in the microwave 4×8 minutes at 400 W and then the solvent is evaporated down in vacuo. The residue is mixed with water and 1N sodium hydroxide solution and extracted with diethylether. The organic phase is dried over sodium sulphate, the solvent is evaporated in vacuo. Yield: 19.6 g (52% of theory).

b) Preparation of 2-[2-(N,N-dimethylamino)ethyloxy]-benzoic acid amidoxime 14 g of hydroxylamine hydrochloride are dissolved in 100 ml of water and mixed with 16.8 g of sodium hydrogen carbonate, batchwise, with stirring. To this mixture is added a solution of 19.0 g of 2-(N,N-dimethylamino)ethyloxy-benzoic acid nitrile in 150 ml of ethanol and the resulting mixture is refluxed for 5 hours. Then the ethanol is evaporated off in vacuo and the residue is extracted twice with diethylether. The combined ether phases are dried over sodium sulphate and concentrated by evaporation. The residue (16 g of=72% of theory) is used in the reaction of cyclisation without further purification.

c) Preparation of 3-{2-[2-(N,N-dimethylamino)ethyl]oxy-phenyl}-5-phenyl-1,2,4-oxadiazole 4.46 g of 2-(N,N-dimethylamino)ethyloxy-benzoic acid amidoxime and 5.44 g of methyl benzoate are dissolved in 150 ml of absolute ethanol, mixed with 2.3 g of sodium and heated in the microwave twice for 11 minutes (with a 5 minute break) at 300 W. The reaction mixture is concentrated by evaporation in vacuo, the residue is mixed with water and extracted with ethyl acetate. The organic phase is dried over sodium sulphate, the solvent is evaporated in vacuo and the residue is chromatographed on silica gel with ethyl acetate/isopropanol (70:30, mixed with 2.5% of a 25% ammonia solution). The base thus obtained is dissolved in anhydrous ethanol, acidified with ethereal HCl and precipitated with diethyl ether. The residue is recrystallised from anhydrous ethanol and diethylether. Yield: 2.5 g (36% of theory). m.p.: 174–175° C.

EXAMPLE 4

5-{2-[2-(Morpholino)ethyl]oxy-phenyl}-3-phenyl-1,2,4-oxadiazole

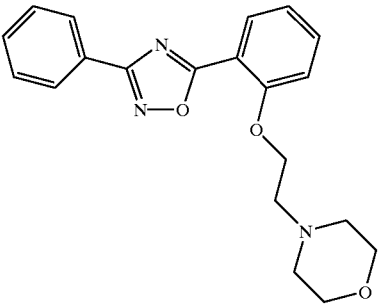

2.38 g of 5-(2-hydroxyphenyl)-3-phenyl-1,2,4-oxadiazole are dissolved in 100 ml of anhydrous dioxane and stirred with 0.3 g of 80% sodium hydride suspension in oil for 15 minutes at 25–30° C. To this solution is added 75 ml of absolute dioxane, mixed with 3.72 g of 2-(morpholino)ethylchloride hydrochloride and 0.6 g of 80% sodium hydride suspension in oil. This solution is also stirred for 15 minutes at 25–30° C. The combined solutions are heated to 100° C. for 6 hours and then concentrated by evaporation in vacuo. The residue is mixed with water and 20 ml of 1N sodium hydroxide solution and extracted with ethyl acetate. The organic phase is dried over sodium sulphate, the solvent is distilled off in vacuo and the residue is chromatographed on silica gel with ethyl acetate/isopropanol (70:30, mixed with 1.5% of a 25% ammonia solution). The base thus obtained is dissolved in anhydrous ethanol, acidified with ethereal HCl and precipitated with diethyl ether. The residue is recrystallised from anhydrous ethanol and diethylether. Yield: 1.9 g (49% of theory). m.p.: 194–195° C.

EXAMPLE 5

5-{2-[2-(4-methylpiperazin-1-yl)ethyl]oxy-phenyl}-3-phenyl-1,2,4-oxadiazole

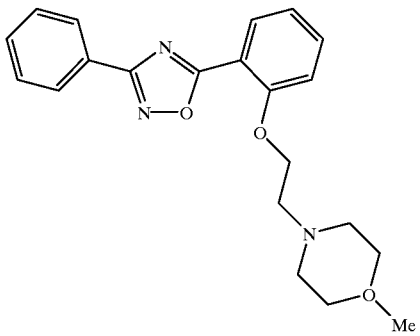

a) Preparation of 5-[2-(2-bromoethyl)oxy-phenyl]-3-phenyl-1,2,4-oxadiazole 1.85 g of 5-(2-hydroxyphenyl)-3-phenyl-1,2,4-oxadiazole are dissolved in 80 ml of methylethylketone, mixed with 5 ml of 1,2-dibromoethane, 6 g of potassium carbonate and 0.1 g of potassium iodide. The mixture is refluxed for 12 hours and after cooling the precipitate is filtered off. The organic phase is evaporated down in vacuo and chromatographed on silica gel first with toluene, then with dichloromethane as eluant. Yield: 2.3 g (86% of theory).

b) Preparation of 5-{2-[2-(4-methylpiperazin-1-yl)ethyl]oxy-phenyl}-3-phenyl-1, 2,4-oxadiazole 1.72 g of 5-[2-(2-bromoethyl)oxy-phenyl]-3-phenyl-1,2,4-oxadiazole are dissolved in 50 ml of anhydrous dioxane and mixed with 2 g of N-methylpiperazine. The solution is refluxed for one hour and then concentrated by evaporation in vacuo. The residue is chromatographed on silica gel with dichloromethane/methanol (90/10). The base thus obtained is dissolved in anhydrous ethanol, acidified with ethereal HCl and precipitated with diethyl ether. The residue is recrystallised from anhydrous ethanol and diethylether. Yield: 1.7 g (78% of theory). m.p.: 251–253° C.

EXAMPLE 6

5-phenyl-3-[2-(4-methylpiperazin-1-yl)-phenyl]-1,2,4-oxadiazole

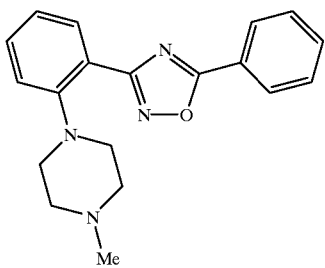

a) Preparation of 1-(2-cyanophenyl)piperazine
b) (analogously to G. E. Martin, R. J. Elgin, J. R. Mathiasen, C. B. Davis, J. M. Kesslick, J. Med. Chem. 32 (1989) 1052–1056)

b) Preparation of 1-(2-cyanophenyl)-4-methylpiperazine 7.48 g of 1-(2-cyanophenyl)-piperazine are refluxed for one hour with 30 ml of formaldehyde and 30 ml of formic acid. The solvents are evaporated in vacuo and the residue is taken up in ether and mixed with water. The mixture is made alkaline with 20% sodium hydroxide solution, saturated with potassium carbonate and extracted with ether. The organic phase is dried over sodium sulphate and concentrated by evaporation in vacuo. To purify the residue it is chromatographed on silica gel with ethyl acetate/isopropanol (70:30, mixed with 1% of a 25% ammonia solution). Yield: 6.7 g (83% of theory).

c) The Amidoximes are Prepared Using the Procedure Described for Example 3b d) The 1,2,4-oxadiazoles are Prepared Using the Procedure Described for Example 3c

EXAMPLE 7

3-phenyl-5-[2-(piperazin-1-yl)-phenyl]-1,2,4-oxadiazole

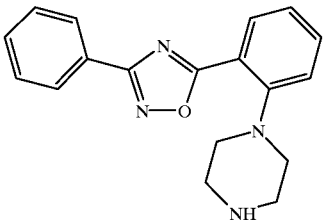

a) Preparation of methyl 2-(piperazin-1-yl)-benzoate (analogously to G. S. Poindexter, M. A. Bruce, K. L. LeBoulluec, I. Monkovic, Tetrahedron Lett. 35 (1994) 7331–7334)

b) Preparation of 5-[2-(piperazin-1-yl)-phenyl]-3-phenyl-1,2,4-oxadiazole 1.36 g of benzoic acid amidoxime and 2.34 g of ethyl 2-(piperazin-1-yl)-benzoate maleinate are mixed with 0.92 g of sodium in 100 ml of anhydrous ethanol and heated in the microwave 6×30 minutes (with a 5 minute break each time) at 350 W. After cooling, the solvent is concentrated by evaporation in vacuo and the residue is extracted with dichloromethane against water. The organic phase is dried over sodium sulphate and concentrated by evaporation in vacuo. The residue is chromatographed on silica gel with ethyl acetate/isopropanol (70:30, mixed with 5% of a 25% ammonia solution). Yield: 90 mg (3% of theory). m.p.: 254–255° C.

EXAMPLE 8

5-{2-[2-(N,N-Dimethylamino)ethyl]oxy-phenyl}-3-(4-hydroxyphenyl)-1,2,4-oxadiazole

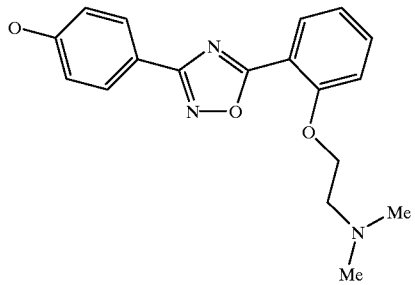

a) Preparation of methyl 2-[2-(N,N-dimethylamino)ethyl]oxy-benzoate 15.2 g of methyl salicylate are dissolved in 200 ml of anhydrous acetonitrile and stirred with 4.4 g of 60% sodium hydride suspension in oil at ambient temperature for 60 minutes. To this solution is added 200 ml of absolute acetonitrile, then it is mixed with 17.4 g of 2-(N,N-dimethylamino)ethylchloride hydrochloride and 5.2 g of 60% sodium hydride suspension in oil. This solution is also stirred for 60 minutes at ambient temperature. The combined solutions are refluxed for 1 hour and then evaporated down in vacuo. The residue is mixed with water and extracted with ethyl acetate. The organic phase is dried over sodium sulphate, the solvent is distilled off in vacuo and the residue is chromatographed on silica gel with ethyl acetate/methanol (1:1). In this way, 14.6 g of a yellow oil are obtained (65% of theory).

b) Preparation of 2-[2-(N,N-dimethylamino)ethyl]oxy-benzoic acid 4.4 g of methyl 2-[2-(N,N-dimethylamino)ethyl]oxy-benzoate are heated in the microwave for 15 minutes at 300 W with 30 ml of 5N hydrochloric acid. The mixture is extracted with ethyl acetate, the aqueous phase is concentrated by evaporation and recrystallised from acetonitrile/ether. Yield: 4.2 g (86% of theory).

c) Preparation of 5-{2-[2-(N,N-dimethylamino)ethyl]oxy-phenyl}-3-(4-hydroxy-phenyl)-1,2,4-oxadiazole 2,45 g of 2-[2-(N,N-dimethylamino)ethyl]oxy-benzoic acid are dissolved with 1.91 g of N-ethyl-N-dimethylaminopropyl)carbodiimide hydrochloride and catalytic amounts of hydroxybenzotriazole in 50 ml of DMF. After 15 minutes 1.52 g of 4-hydroxybenzoic acid amidoxime are added and the mixture is heated for 15 minutes at 700 W in the microwave. It is concentrated by evaporation, the residue is taken up in ethyl acetate, washed with water, dried over sodium sulphate and concentrated by evaporation in vacuo. The residue is filtered over silica gel with ethanol and converted into the salt as described above. Yield: 1.1 g (29% of theory). m.p.: 170° C. (decomposition).

EXAMPLE 9

5-{2-[(Carboxamido)methyl]oxy-phenyl}-3-phenyl-1,2,4-oxadiazole

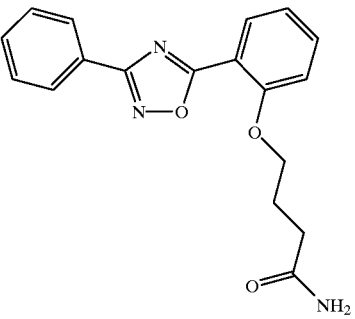

3.57 g of 5-(2-hydroxyphenyl)-3-phenyl-1,2,4-oxadiazole are dissolved in 70 ml of anhydrous DMF and stirred with 0.6 g of 60% sodium hydride suspension in oil for 30 minutes at 25–30° C. To this solution are added 1.4 g of 2-chloroacetamide and the mixture is stirred for 2 hours at 100° C. Then the solvent is evaporated down in vacuo. The residue is mixed with water and suction filtered. The precipitate is decocted successively with methanol and ethyl acetate. Yield: 3.3 g (75% f theory). Melting point 249–251° C.

EXAMPLE 10

5-{2-[2-(Carboxamido)ethyl]oxy-phenyl}-3-phenyl-1,2,4-oxadiazole

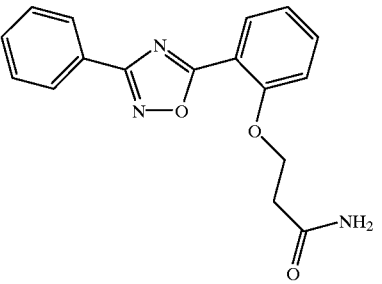

a) Preparation of 5-{2-[2-(1,3-dioxan-2-yl)ethyl]oxy-phenyl}-3-phenyl-1,2,4-oxadiazole 4.1 g of 5-(2-hydroxy)-3-phenyl-1,2,4-oxadiazole are dissolved in 60 ml of anhydrous DMF and mixed with 0.688 g of 60% sodium hydride suspension in oil. To this mixture are added 3.15 g of 2-(2-bromoethyl)-1,3-dioxane and the resulting mixture is stirred for 4 hours at 100° C. After cooling the solvent is evaporated in vacuo and the residue is combined with water. It is extracted with ethyl acetate, the organic phase is dried over sodum sulphate and evaporated down in vacuo. The solution remaining is chromatographed on silica gel with ethyl acetate. Yield: 2.5 g (41% of theory).

b) Preparation of 5-{2-[2-(carboxy)ethyl]oxy-phenyl}-3-phenyl-1,2,4-oxadiazole 2.5 g of 5-{2-[2-(1,3-dioxan-2-yl)ethyl]oxy-phenyl}-3-phenyl-1,2,4-oxadiazole are dissolved in 50 ml of acetone and at 0° C. a solution of chromium(VI)oxide in 30% sulphuric acid is added dropwise thereto. The mixture is then stirred for a further 20 hours at 20–23° C. and then 25 ml of isopropanol are added with cooling at 5° C. The mixture is added to a suspension of 100 ml of dichloromethane and 100 ml of water and the organic phase is separated off. The aqueous phase is extracted once more with dichloromethane and the combined organic solutions are again extracted with water. The extract is dried over sodium sulphate, evaporated down in vacuo and the residue is chromatographed on silica gel with dichloromethane/methanol (97:3). The product is recrystallised from ethyl acetate. Yield: 0.23 g (11% of theory), melting point 170–171° C.

c) Preparation of 5-{2-[2-(carboxamido)ethyl]oxy-phenyl}-3-phenyl-1,2,4-oxadiazole 0.8 g of 5-{2-[2-(carboxy)ethyl]oxy-phenyl}-3-phenyl-1,2,4-oxadiazole are dissolved in 40 ml of anhydrous dichloromethane and cooled to 0° C. 2 ml of oxalyl chloride dissolved in 5 ml of anhydrous dichlormethane are then added to this solution, and the mixture is stirred for 1.5 hours at 20° C. The solvent is evaporated in vacuo and 30 ml of anhydrous dichloromethane are added. Ammoniacal dichloromethane solution is added with cooling until the reaction medium reacts basically. It is left to stand for 14 hours, water is added, the precipitate formed and the dichloromethane phase are separated off, and the organic phase is dried over sodium sulphate. After evaporation, the residue amounts to 0.7 g. This is chromatographed on silica gel with dichloromethane/methanol (98:2) and the product is recrystallised from ethyl acetate. Yield: 0.24 g (33% of theory), melting point 137–138° C.

The following compounds were prepared analogously to the processes described hereinbefore:

TABLE 1

Oxadiazoles of general formula (Ia)

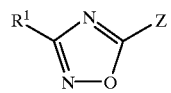

(Ia)

| Example | R¹ | Z | m.p. [° C.] | chemical name |
|---|---|---|---|---|
| 11 | phenyl | 3-[2-(NMe₂)ethyloxy]phenyl | 220–221ª | 5-{3-[2-(N,N-Dimethylamino)-ethyl[oxy-phenyl}-3-phenyl-1,2,4-oxadiazole |
| 12 | phenyl | 2-[2-(NEt₂)ethyloxy]phenyl | 157–158ª | 5-{2-[2-(N,N-Diethylamino)ethyl]-oxy-phenyl}-3-phenyl-1,2,4-oxadiazole |
| 13 | phenyl | 2-[2-(N-pyrrolidinyl)ethyloxy]phenyl | 164–165ª | 5-{2-[2-(N-Pyrrolidinyl)ethyl]oxy-phenyl}-3-phenyl-1,2,4-oxadiazole |
| 14 | phenyl | 2-[2-(N-piperidinyl)ethyloxy]phenyl | 194–195ª | 5-{2-[2-(N-Piperidinyl)ethyl]oxy-phenyl}-3-phenyl-1,2,4-oxadiazole |
| 15 | phenyl | 2-[2-(N-ethyl-N-phenylamino)ethyloxy]phenyl | 141–142ª | 5-{2-[2-(N-ethyl-N-phenylamino)-ethyl]oxy-phenyl}-3-phenyl-1,2,4-oxadiazole |
| 16 | phenyl | 2-(cyanomethyloxy)phenyl | 104–105 | 5-[2-(Cyanomethyl)oxy-phenyl]-3-phenyl-1,2,4-oxadiazole |

TABLE1-continued

Oxadiazoles of general formula (Ia)

| Example | R¹ | Z | m.p. [° C.] | chemical name |
|---|---|---|---|---|
| 17 | 4-Me-C₆H₄– | 2-Me-C₆H₃-O-CH₂CH₂-NMe₂ | 205[a] | 5-{2-[2-(N,N-Dimethylamino)-ethyl]oxy-phenyl}-3-(4-methyl-phenyl)-1,2,4-oxadiazole |
| 18 | 4-Cl-C₆H₄– | 2-Me-C₆H₃-O-CH₂CH₂-NMe₂ | 211[a] | 5-{2-[2-(N,N-Dimethylamino)-ethyl]oxy-phenyl}-3-(4-chlor-phenyl)-1,2,4-oxadiazole |
| 19 | 4-MeO-C₆H₄– | 2-Me-C₆H₃-O-CH₂CH₂-NMe₂ | 194[a] | 5-{2-[2-(N,N-Dimethylamino)-ethyl]oxy-phenyl}-3-(4-methoxy-phenyl)-1,2,4-oxadiazole |
| 20 | C₆H₅– | 2-Me-C₆H₃-O-CH₂CH₂-NH-CH₂Ph | 167–168[a] | 5-{2-[2-(N-benzylamino)ethyl]-oxy-phenyl}-3-phenyl-1,2,4-oxa-diazole |
| 21 | C₆H₅– | 2-Me-C₆H₃-O-CH₂CH₂-NH-CH(Me)₂ | 185–186[a] | 5-{2-[2-(N-Isopropylamino)ethyl]-oxy-phenyl}-3-phenyl-1,2,4-oxa-diazole |
| 22 | C₆H₅– | 2-Me-C₆H₃-O-CH₂CH₂-NHMe | 205–206[a] | 5-{2-[2-(N-methylamino)ethyl]-oxy-phenyl}-3-phenyl-1,2,4-oxa-diazole |
| 23 | C₆H₅– | 2-Me-C₆H₃-O-CH₂CH₂-NHEt | 161–162[a] | 5-{2-[2-(N-ethylamino)ethyl]-oxy-phenyl}-3-phenyl-1,2,4-oxa-diazole |
| 24 | C₆H₅– | 2-Me-C₆H₃-O-CH₂CH₂-NH₂ | 212–214[a] | 5-[2-(2-aminoethyl)oxy-phenyl]-3-phenyl-1,2,4-oxadiazole |

TABLE 1-continued

Oxadiazoles of general formula (Ia)

$$\text{(Ia)}$$

| Example | R¹ | Z | m.p. [° C.] | chemical name |
|---|---|---|---|---|
| 25 | phenyl | 4-[2-(NMe₂)ethyloxy]phenyl | 219–220[a] | 5-{4-[2-(N,N-Dimethylamino)-ethyl]oxy-phenyl}-3-phenyl-1,2,4-oxadiazole |
| 26 | 3,4-dichlorophenyl | 2-[2-(NMe₂)ethyloxy]phenyl | 233[a] | 5-{2-[2-(N,N-Dimethylamino)-ethyl]oxy-phenyl}-3-(3,4-dichloro-phenyl)-1,2,4-oxadiazole |
| 27 | 2-chlorophenyl | 2-[2-(NMe₂)ethyloxy]phenyl | 166–168[a] | 5-{2-[2-(N,N-Dimethylamino)-ethyl]oxy-phenyl}-3-(2-chloro-phenyl)-1,2,4-oxadiazole |
| 28 | 2,4-dichlorophenyl | 2-[2-(NMe₂)ethyloxy]phenyl | 185[a] | 5-{2-[2-(N,N-Dimethylamino)-ethyl]oxy-phenyl}-3-(2,4-dichloro-phenyl)-1,2,4-oxadiazole |
| 29 | Me | 2-[2-(NMe₂)ethyloxy]phenyl | 94[b] (decomp) | 5-{2-[2-(N,N-Dimethylamino)-ethyl]oxy-phenyl}-3-methyl-1,2,4-oxadiazole |
| 30 | 4-(4-hydroxyphenyl)oxy-phenyl | 2-[2-(NMe₂)ethyloxy]phenyl | 120–122[a] | 5-{2-[2-(N,N-Dimethylamino)-ethyl]oxy-phenyl}-3-[4-(4-hydroxyphenyl)oxy-phenyl[-1,2,4-oxadiazole |
| 31 | benzyl | 2-[2-(NMe₂)ethyloxy]phenyl | 150–153[a] | 5-{2-[2-(N,N-Dimethylamino)-ethyl]oxy-phenyl}-3-benzyl-1,2,4-oxadiazole |
| 32 | 2-[2-(NMe₂)ethyloxy]phenyl | 2-[2-(NMe₂)ethyloxy]phenyl | 167[a] | 5-{2-[2-(N,N-Dimethylamino)-ethyl]oxy-phenyl}-3-{2-[2-(N,N-dimethylamino)ethyl]oxy-phenyl}-1,2,4-oxadiazole |

TABLE 1-continued

Oxadiazoles of general formula (Ia)

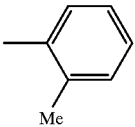

(Ia)

| Example | R¹ | Z | m.p. [° C.] | chemical name |
|---|---|---|---|---|
| 33 | 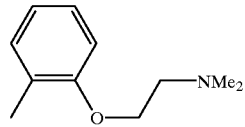 | 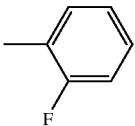 | 196–197[a] | 5-{2-[2-(N,N-Dimethylamino)-ethyl[oxy-phenyl}-3-(2-methyl-phenyl)-1,2,4-oxadiazole |
| 34 | 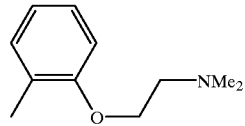 | 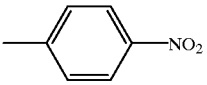 | 199[a] | 5-{2-[2-(N,N-Dimethylamino)-ethyl[oxy-phenyl}-3-(2-fluoro-phenyl)-1,2,4-oxadiazole |
| 35 | 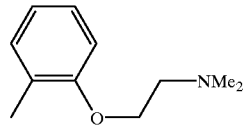 | 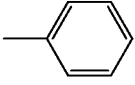 | 250[a] (decomp) | 5-[2-(2-N,N-Dimethylamino-ethyl-oxy)phenyl]-3-(4-nitro-phenyl)-1,2,4-oxadiazole |
| 36 | 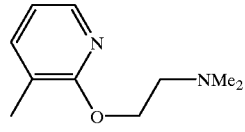 | 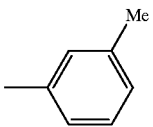 | 273–274[a] | 5-{2-[2-(N,N-Dimethylamino)-ethyl]oxy-pyridin-3-yl}-3-phenyl-1,2,4-oxadiazole |
| 37 | 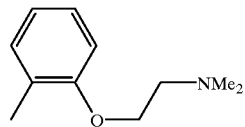 | 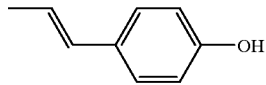 | 166–167[a] | 5-{2-[2-(N,N-Dimethylamino)-ethyl]oxy-phenyl}-3-(3-methyl-phenyl)-1,2,4-oxadiazole |
| 38 | 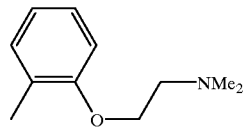 | 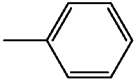 | 102[a] (decomp) | 5-{2-[2-(N,N-Dimethylamino)-ethyl]oxy-phenyl}-3-[2-(4-hydroxyphenyl)-vinyl]-1,2,4-oxadiazole |
| 39 | 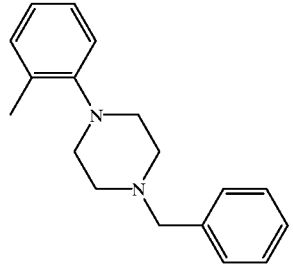 | 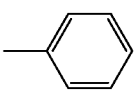 | 212–214[a] | 5-[2-(4-benzylpiperazin-1-yl)phe-nyl]-3-phenyl-1,2,4-oxadiazole |
| 40 | 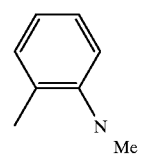 |  | 218–220[a] | 5-[2-(4-methylpiperazin-1yl)-phenyl]-3-phenyl-1,2,4-oxadiazole |

TABLE 1-continued

Oxadiazoles of general formula (Ia)

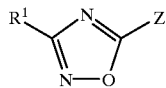

(Ia)

| Example | R¹ | Z | m.p. [° C.] | chemical name |
|---|---|---|---|---|
| 41 | 4-methylpyridyl | 2-(2-(NMe₂)ethoxy)phenyl | 220ᵃ (decomp) | 5-{2-[2-(N,N-Dimethylamino)-ethyl]oxy-phenyl}-3-(4-pyridyl)-1,2,4-oxadiazole |
| 42 | 2-methylthienyl | 2-(2-(NMe₂)ethoxy)phenyl | 186ᵃ | 5-{2-[2-(N,N-Dimethylamino)-ethyl]oxy-phenyl}-3-(2-thienyl)-1,2,4-oxadiazole |
| 43 | 2-methylpyridyl | 2-(2-(NMe₂)ethoxy)phenyl | 185ᵃ | 5-{2-[2-(N,N-Dimethylamino)-ethyl]oxy-phenyl}-3-(2-pyridyl)-1,2,4-oxadiazole |
| 44 | 3-(CF₃)phenyl | 2-(2-(NMe₂)ethoxy)phenyl | 185ᵃ | 5-{2-[2-(N,N-Dimethylamino)-ethyl]oxy-phenyl}-3-(3-rifluoromethylphenyl)-1,2,4-oxadiazole |
| 45 | 4-fluorophenyl | 2-(2-(NMe₂)ethoxy)phenyl | 216–220ᵃ | 5-{2-[2-(N,N-Dimethylamino)-ethyl]oxy-phenyl}-3-(4-fluoro-phenyl)-1,2,4-oxadiazole |
| 46 | phenyl | 1-(2-(NMe₂)ethoxy)naphth-2-yl | 235–236ᵃ | 5-{1-[2-(N,N-Dimethylamino)-ethyl]oxy-naphth-2-yl}-3-phenyl-1,2,4-oxadiazole |
| 47 | 4-aminophenyl | 2-(2-(NMe₂)ethoxy)phenyl | 245ᵃ | 5-{2-[2-(N,N-Dimethylamino)-ethyl]oxy-phenyl}-3-(4-amino-phenyl)-1,2,4-oxadiazole |
| 48 | 3-bromophenyl | 2-(2-(NMe₂)ethoxy)phenyl | 192–194ᵃ | 5-{2-[2-(N,N-Dimethylamino)-ethyl]oxy-phenyl}-3-(3-bromophenyl)-1,2,4-oxadiazole |
| 49 | 4-(NMe₂)phenyl | 2-(2-(NMe₂)ethoxy)phenyl | 225–230ᵃ | 5-{2-[2-(N,N-Dimethylamino)-ethyl]oxy-phenyl}-3-[4-(N,N-dimethylamino)phenyl]-1,2,4-oxadiazole |

TABLE 1-continued

Oxadiazoles of general formula (Ia)

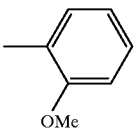

(Ia)

| Example | R¹ | Z | m.p. [° C.] | chemical name |
|---|---|---|---|---|
| 50 | 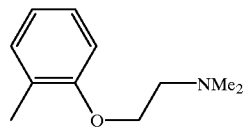 | 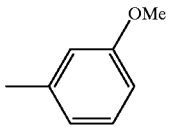 | 197–199[a] | 5-{2-[2-(N,N-Dimethylamino)-ethyl]oxy-phenyl}-3-(2-methoxy)-phenyl)-1,2,4-oxadiazole |
| 51 | 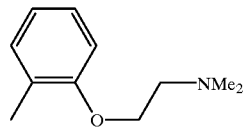 | 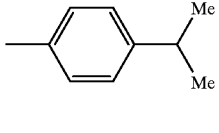 | 148[a] | 5-{2-[2-(N,N-Dimethylamino)-ethyl]oxy-phenyl}-3-(3-methoxy)-phenyl)-1,2,4-oxadiazole |
| 52 | 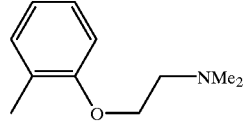 | 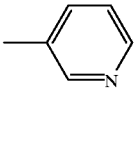 | 157–158[a] | 5-{2-[2-(N,N-Dimethylamino)-ethyl]oxy-phenyl}-3-(4-isopropyl-phenyl)-1,2,4-oxadiazole |
| 53 | 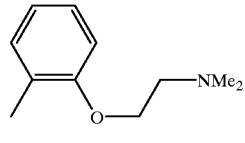 | 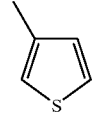 | 188–189[a] | 5-{2-[2-(N,N-Dimethylamino)-ethyl]oxy-phenyl}-3-(3-pyridyl)-1,2,4-oxadiazole |
| 54 | 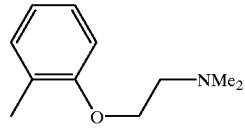 | 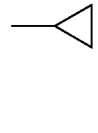 | 186–189[a] | 5-{2-[2-(N,N-Dimethylamino)-ethyl]oxy-phenyl}-3-(3-thienyl)-1,2,4-oxadiazole |
| 55 | 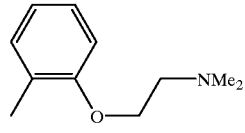 | 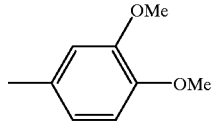 | 154–155[a] | 5-{2-[2-(N,N-Dimethylamino)-ethyl]oxy-phenyl}-3-cyclopropyl-1,2,4-oxadiazole |
| 56 | 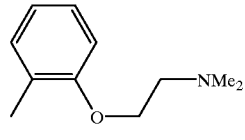 | 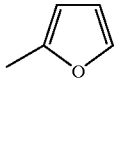 | 210–213[a] | 5-{2-[2-(N,N-Dimethylamino)-ethyl]oxy-phenyl}-3-(3,4-dimethoxyphenyl)-1,2,4-oxadiazole |
| 57 | 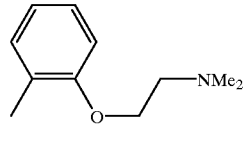 | 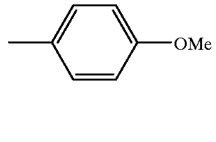 | 176–178[a] | 5-{2-[2-(N,N-Dimethylamino)-ethyl]oxy-phenyl}-3-(2-furyl)-1,2,4-oxadiazole |
| 58 | 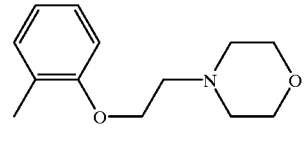 |  | 189–191[a] | 5-{2-[2-(N-Morpholino)ethyl]oxy-phenyl}-3-(4-methoxyphenyl)-1,2,4-oxadiazole |

TABLE 1-continued

Oxadiazoles of general formula (Ia)

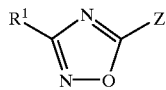

(Ia)

| Example | R¹ | Z | m.p. [° C.] | chemical name |
|---|---|---|---|---|
| 59 | 3-chlorophenyl | 2-[2-(N,N-dimethylamino)ethyl]oxy-phenyl | 152[a] | 5-{2-[2-(N,N-Dimethylamino)-ethyl]oxy-phenyl}-3-(3-chlorophenyl)-1,2,4-oxadiazole |
| 60 | 1,5-dimethylpyrrol-2-yl | 2-[2-(N,N-dimethylamino)ethyl]oxy-phenyl | 169–171[a] | 5-{2-[2-(N,N-Dimethylamino)-ethyl]oxy-phenyl}-3-(1,5-dimethylpyrrol-2-yl)-1,2,4-oxadiazole |
| 61 | 4-methylphenyl | 2-[2-(N-morpholino)ethyl]oxy-phenyl | 197–199[a] | 5-{2-[2-(N-Morpholino)ethyl]oxy-phenyl}-3-(4-methylphenyl)-1,2,4-oxadiazole |
| 62 | 4-ethoxyphenyl | 2-[2-(N,N-dimethylamino)ethyl]oxy-phenyl | 190–193[a] | 5-{2-[2-(N,N-Dimethylamino)-ethyl]oxy-phenyl}-3-(4-ethoxy-phenyl)-1,2,4-oxadiazole |
| 63 | phenyl | 2-[3-(N-morpholino)propyl]oxy-phenyl | 199–214[a] | 5-{2-[3-(N-Morpholino)propyl]oxy-phenyl}-3-phenyl-1,2,4-oxadiazole |
| 64 | 2-bromophenyl | 2-[2-(N,N-dimethylamino)ethyl]oxy-phenyl | 175–178[a] | 5-{2-[2-(N,N-Dimethylamino)-ethyl]oxy-phenyl}-3-(2-bromo-phenyl)-1,2,4-oxadiazole |
| 65 | 4-trifluoromethylphenyl | 2-[2-(N,N-dimethylamino)ethyl]oxy-phenyl | 208–212[a] | 5-{2-[2-(N,N-Dimethylamino)-ethyl]oxy-phenyl}-3-(4-trifluorome-thylphenyl)-1,2,4-oxadiazole |
| 66 | 4-ethylphenyl | 2-[2-(N,N-dimethylamino)ethyl]oxy-phenyl | 170–175[a] | 5-{2-[2-(N,N-Dimethylamino)-ethyl]oxy-phenyl}-3-(4-ethyl-phenyl)-1,2,4-oxadiazole |
| 67 | phenyl | 2-[2-(N,N-dimethylamino)ethyl]oxy-4-methyl-phenyl | 177–178[a] | 5-{2-[2-(N,N-Dimethylamino)-ethyl]oxy-4-methyl-phenyl}-3-phenyl-1,2,4-oxadiazole |

TABLE 1-continued

Oxadiazoles of general formula (Ia)

(Ia)

$$\underset{\text{N}-\text{O}}{\overset{R^1\diagdown\underset{\|}{N}\diagup Z}{}}$$

| Example | R¹ | Z | m.p. [° C.] | chemical name |
|---|---|---|---|---|
| 68 | 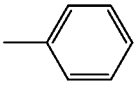 | 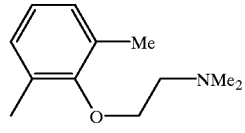 | 174–175[a] | 5-{2-[2-(N,N-Dimethylamino)-ethyl]oxy-3-methyl-phenyl}-3-phenyl-1,2,4-oxadiazole |
| 69 | 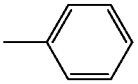 | 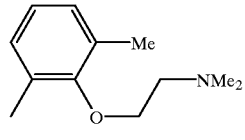 | 219[a] (decomp) | 5-{2-[2-(N,N-Dimethylamino)-ethyl]oxy-4-methoxy-phenyl}-3-phenyl-1,2,4-oxadiazole |
| 70 | 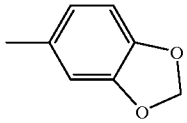 | 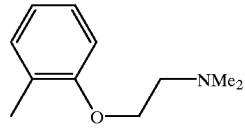 | 216–219[a] | 5-{2-[2-(N,N-Dimethylamino)-ethyl]oxy-phenyl}-3-(1,3-benzodioxol-5-yl)-1,2,4-oxadiazole |
| 71 | 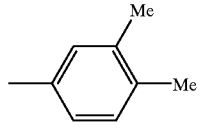 | 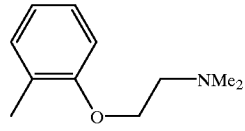 | 213–216[a] | 5-{2-[2-(N,N-Dimethylamino)-ethyl]oxy-phenyl}-3-(3,4-dimethyl-phenyl)-1,2,4-oxadiazole |
| 72 | 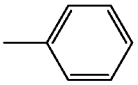 | 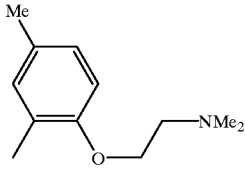 | 186–189[a] | 5-{2-[2-(N,N-Dimethylamino)-ethyl]oxy-5-methyl-phenyl}-3-phenyl-1,2,4-oxadiazole |
| 73 | 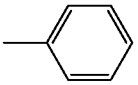 | 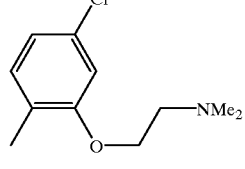 | 205–207[a] | 5-{2-[2-(N,N-Dimethylamino)-ethyl]oxy-4-chloro-phenyl}-3-phenyl-1,2,4-oxadiazole |
| 74 | 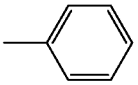 | 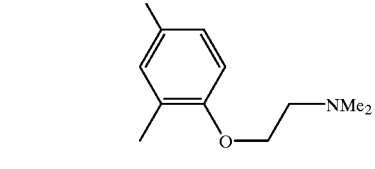 | 197–200[a] | 5-{2-[2-(N,N-Dimethylamino)-ethyl]oxy-5-chloro-phenyl}-3-phenyl-1,2,4-oxadiazole |
| 75 | 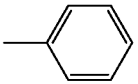 | 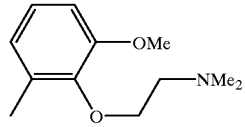 | 190–197[a] | 5-{2-[2-(N,N-Dimethylamino)-ethyl]oxy-3-methoxy-phenyl}-3-phenyl-1,2,4-oxadiazole |

TABLE 1-continued

Oxadiazoles of general formula (Ia)

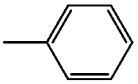

(Ia)

| Example | R¹ | Z | m.p. [° C.] | chemical name |
|---|---|---|---|---|
| 76 | 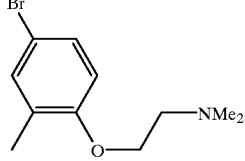 | 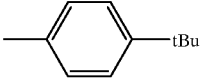 | 211–212[a] | 5-{2-[2-(N,N-Dimethylamino)-ethyl]oxy-5-bromo-phenyl}-3-phenyl-1,2,4-oxadiazole |
| 77 | 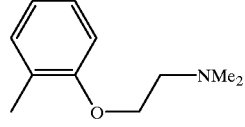 | 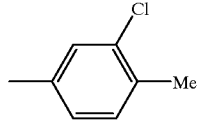 | 173–175[a] | 5-{2-[2-(N,N-Dimethylamino)-ethyl]oxy-phenyl}-3-(4-tert-butyl-phenyl)-1,2,4-oxadiazole |
| 78 | 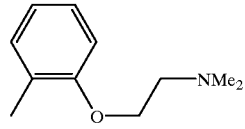 |  | 217–220[a] | 5-{2-[2-(N,N-Dimethylamino)-ethyl]oxy-phenyl}-3-(3-chloro-4-methyl-phenyl)-1,2,4-oxadiazole |
| 79 | 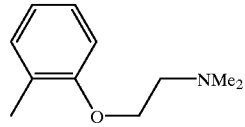 | 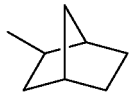 | 157[a] | 5-{2-[2-(N,N-Dimethylamino)-thyl]oxy-phenyl}-3-(2 norbornen-5-yl)-1,2,4-oxadiazole |
| 80 | 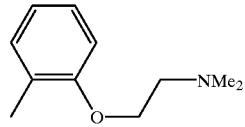 | 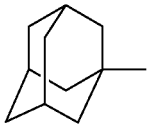 | 170[a] | 5-{2-[2-(N,N-Dimethylamino)-ethyl]oxy-phenyl}-3-(2-norbornanyl)-1,2,4-oxadiazole |
| 81 | 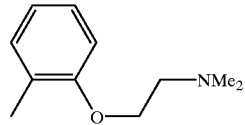 | 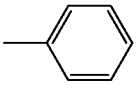 | 247[a] | 5-{2-[2-(N,N-Dimethylamino)-ethyl]oxy-phenyl}-3-(1-adamantyl)-1,2,4-oxadiazole |
| 82 | 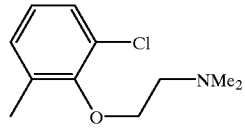 | 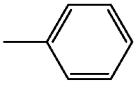 | 188–189[a] | 5-{2-[2-(N,N-Dimethylamino)-ethyl]oxy-3-chlor-phenyl}-3-phenyl-1,2,4-oxadiazole |
| 83 | 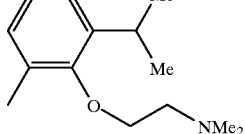 | 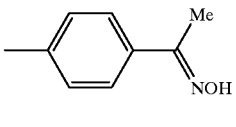 | 218–220[a] | 5-{2-[2-(N,N-Dimethyiamino)-ethyl[oxy-3-isopropyl-phenyl}-3-phenyl-1,2,4-oxadiazole |
| 84 | 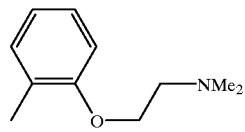 |  | 259–262[a] (decomp) | 5-{2-[2-(N,N-Dimethylamino)-ethyl]oxy-phenyl}-3-[4-(ethyl-1-hydroxyimino)-phenyl]-1,2,4-oxadiazole |

TABLE 1-continued

Oxadiazoles of general formula (Ia)

(Ia)

| Example | R¹ | Z | m.p. [° C.] | chemical name |
|---|---|---|---|---|
| 85 | 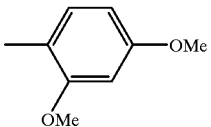 | 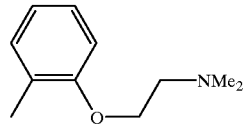 | 180–182[a] | 5-{2-[2-(N,N-Dimethylamino)-ethyl]oxy-phenyl}-3-(2,4-dimethoxyphenyl) 1,2,4oxadiazole |
| 86 |  | 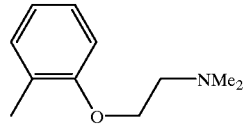 | 105–116[a] | 5-{2-[2-(N,N-Dimethylamino)-ethyl]oxy-phenyl}-3-cyclopentyl-1,2,4-oxadiazole |
| 87 | 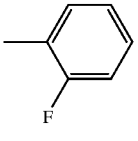 | 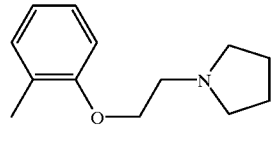 | 175–178[a] | 5-{2-[2-(NPyrrolidino)ethyl]-oxy-phenyl}-3-(2-fluorophenyl)-1,2,4-oxadiazole |
| 88 | 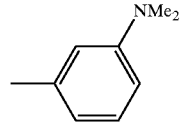 | 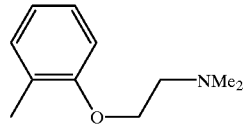 | 188[a] | 5-{2-[2-(N,N-Dimethylamino)-ethyl]oxy-phenyl}-3-[3-(N,N-dimethylamino)phenyl]-1,2,4-oxadiazole |
| 89 | 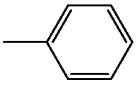 | 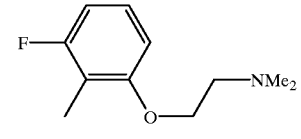 | 111–113[b] | 5-{2-[2-(N,N-Dimethylamino)-ethyl]oxy-6-fluoro-phenyl}-3-phenyl-1,2,4-oxadiazole |
| 90 | 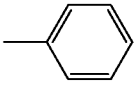 | 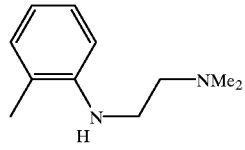 | 204–205[a] | 5-{2-N-[2-(N',N'-Dimethylamino)-ethyl]aminophenyl}-3-phenyl-1,2,4-oxadiazole |
| 91 | 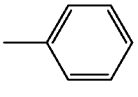 | 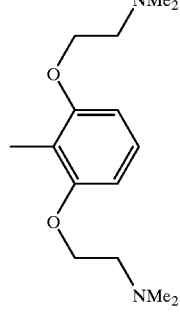 | 220–223[a] (decomp) | 5-{2,6-bis[2-(N,N'-Dimethyl amino) ethyl]oxy-phenyl}-3-phenyl-1,2,4-oxadiazole |
| 92 | 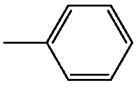 | 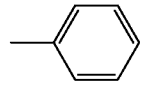 | 110–111 | 3,5-Diphenyl-1,2,4-oxadiazole |

TABLE 1-continued

Oxadiazoles of general formula (Ia)

(Ia)

| Example | R¹ | Z | m.p. [° C.] | chemical name |
|---|---|---|---|---|
| 93 | phenyl | 2-methyl-phenol (OH) | 156–158 | 5-(2-hydroxy-phenyl)-3-phenyl-1,2,4-oxadiazole |
| 94 | phenyl | 2-methyl-anisole (OMe) | 106–107 | 5-(2-methoxy-phenyl)-3-phenyl-1,2,4-oxadiazole |
| 95 | phenyl | 3-methyl-phenol (OH) | 199–200 | 5-(3-hydroxy-phenyl)-3-phenyl-1,2,4-oxadiazole |
| 96 | phenyl | CH₂CH₂NMe₂ | 176[a] | 5-(2-N,N-Dimethylamino-ethyl)-3-phenyl-1,2,4-oxadiazole |
| 97 | phenyl | (CH₂)₄NMe₂ | 183–184[a] | 5-(4-N,N-Dimethylamino-butyl)-3-phenyl-1,2,4-oxadiazole |
| 98 | phenyl | CH₂NMe₂ | 235–236[a] | 5-(N,N-Dimethylamino-methyl)-3-phenyl-1,2,4-oxadiazole |
| 99 | phenyl | (CH₂)₃NMe₂ | 163–164[a] | 5-(3-N,N-Dimethylamino-propyl)-3-phenyl-1,2,4-oxadiazole |
| 100 | phenyl | CH₂OCH₂CH₂NMe₂ | 155–156[a] | 5-(2-N,N-Dimethylamino-ethyl-oxy)methyl-3-phenyl-1,2,4-oxadiazole |
| 101 | phenyl | 2-methyl-N-methylaniline (NHMe) | 154–157[a] | 5-(2-N-methylamino-phenyl)-3-phenyl-1,2,4-oxadiazole |
| 102 | phenyl | 2-(CH₂NMe₂)-phenyl | 221[a] (decomp) | 5-[2-(N,N-Dimethylamino-methyl)-phenyl]-3-phenyl-1,2,4-oxadiazole |

TABLE 1-continued

Oxadiazoles of general formula (Ia)

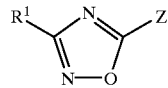

(Ia)

| Example | R¹ | Z | m.p. [° C.] | chemical name |
|---|---|---|---|---|
| 103 | phenyl | 2-methylphenyl-O-CH₂CH₂-NMe₂ | 112–115[a] (decomp) | 5-{2-[2-(N,N-Dimethylamino)-ethyl]oxy-phenyl}methyl-3-phenyl-1,2,4-oxadiazole |
| 104 | phenyl | 2-methylphenyl-S-CH₂CH₂-NMe₂ | 190[a] (decomp) | 5-{2-[2-(N,N-Dimethylamino)-ethyl]mercapto-phenyl}-3-phenyl-1,2,4-oxadiazole |
| 105 | phenyl | 2-methylphenyl-C(O)O-CH₂CH₂-NMe₂ | 102[b] | 5-{2[2-(N,N-Dimethylamino)-ethyl]oxycarbonyl-phenyl}-3-phenyl-1,2,4-oxadiazole |
| 106 | phenyl | 2-methylphenyl-O-CH(Me)-CH₂-NMe₂ | 212–214[a] | 5-{2-[1-(N,N-Dimethylamino-methyl)ethyl]oxy-phenyl}-3-phenyl-1,2,4-oxadiazole |
| 107 | phenyl | 2-methylphenyl-O-CH₂-CH(Me)-NMe₂ | 193–194[a] | -Dimethylamino)-propyl[oxy-phenyl}-3-phenyl-1,2,4-oxadiazole |
| 108 | phenyl | 2-methylphenyl-O-(N-methyl-8-azabicyclo-3-yl) | 241–242[a] | 5-[2-(N-Methyl-8-azabicyclon-3-yl)oxy-phenyl]-3-phenyl-1,2,4-oxadiazole |
| 109 | phenyl | 2-methylphenyl-O-CH₂-(1-methylpyrrolidin-2-yl) | 195–197[a] | 5-{2-[(1-Methylpyrrolidin-2-yl)-methyl]oxy-phenyl}-3-phenyl-1,2,4-oxadiazole |
| 110 | phenyl | 2-methylphenyl-O-(1-methylpyrrolidin-3-yl) | 205–206[a] | 5-{2-(1-Methylpyrrolidin-3-yl)-oxy-phenyl}-3-phenyl-1,2,4-oxadiazole |

TABLE1-continued

Oxadiazoles of general formula (Ia)

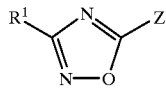

(Ia)

| Example | R¹ | Z | m.p. [° C.] | chemical name |
|---|---|---|---|---|
| 111 | phenyl | 2-methylphenyl-O-(1-azabicyclo[3,2,1]octan-3-yl) | 206–207[a] | 5-{2-(1-Azabicyclo-[3,2,1]-octan-3-yl)oxy-phenyl}-3-phenyl-1,2,4-oxadiazole |
| 112 | phenyl | 2-methylphenyl-O-(1-methylpiperidin-4-yl) | 208–209[a] | 5-{2-(1-Methylpiperidin-4-yl)-oxy-phenyl}-3-phenyl-1,2,4-oxadiazole |
| 113 | phenyl | 2-methylphenyl-O-CH(Ph)-CH(Me)-NMe₂ (2S,1S) | 130–132[a] | 5-{2-[(2(S)-N,N-Dimethylamino)-(1(S)-phenyl)-propyl]oxy-phenyl}-3-phenyl-1,2,4-oxadiazole |
| 114 | phenyl | 2-methylphenyl-O-CH(Ph)-CH(Me)-NMe₂ (2R,1R) | 140–142[a] | 5-{2-[(2(R)-N,N-Dimethylamino)-(1(R)-phenyl)-propyl]oxy-phenyl}-3-phenyl-1,2,4-oxadiazole |
| 115 | phenyl | 2-methylphenyl-O-(2-N,N-dimethylamino-cyclohexyl) | 180–182[a] | 5-{2-(2-N,N-Dimethylamino-cyclohexyl)oxy-phenyl}-3-phenyl-1,2,4-oxadiazole |
| 116 | phenyl | 2-methylphenyl-O-CH₂-C(=O)-NEt₂ | 84–85 | 5-{2-(N,N-Diethylamino-carbonyl)methyloxy-phenyl}-3-phenyl-1,2,4-oxadiazole |

TABLE 1-continued

Oxadiazoles of general formula (Ia)

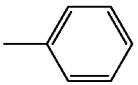

| Example | R¹ | Z | m.p. [° C.] | chemical name |
|---|---|---|---|---|
| 117 | 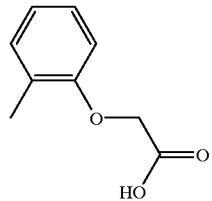 | 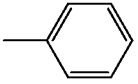 | 175–176 | 5-[2-(Carboxymethyl)oxy-phenyl]-3-phenyl-1,2,4-oxadiazole |
| 118 | 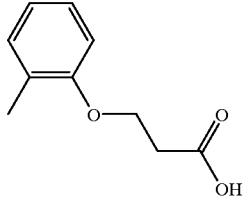 | 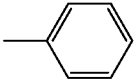 | 170–171 | 5-[2-(2-Carboxyethyl)oxy-phenyl]-3-phenyl-1,2,4-oxadiazole |
| 119 | 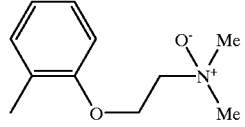 | 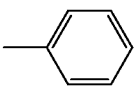 | 162–163 | 5-{2-[2-(N,N-Dimethyl-N-oxido-amino)ethyl]oxy-phenyl}-3-phenyl-1,2,4-oxadiazole |
| 120 | 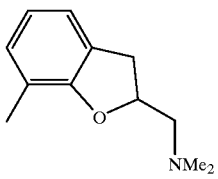 | 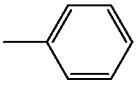 | 236–237[a] | 5-[2-N,N-Dimethylaminomethyl-2,3-dihydro-benzo[b]furan-7-yl]-3-phenyl-1,2,4-oxadiazole |
| 121 | 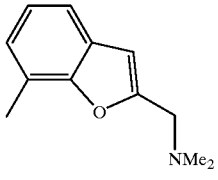 | 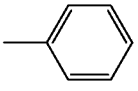 | 252–253[a] | 5-[2-N,N-Dimethylaminomethyl-benzo[b]furan-7-yl]-3-phenyl-1,2,4-oxadiazole |
| 137 | 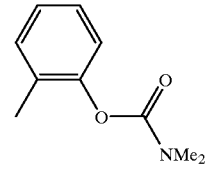 |  | 120–121 | 5-[2-(N,N-Dimethylamino)-carbonyloxy-phenyl]-3-phenyl-1,2,4-oxadiazole |

[a]hydrochloride
[b]fumarate

TABLE 2

Oxadiazoles of general formula (Ib)

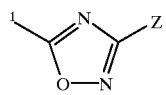

(Ib)

| Example | R¹ | Z | m.p. [° C.] | chemical name |
|---|---|---|---|---|
| 122 | phenyl | 2-methylphenyl-N-piperazine-N'-benzyl | 122–123 | 3-[2-(4-benzylpiperazin-1-yl)-phenyl]-5-phenyl-1,2,4-oxadiazole |
| 123 | 3-methylphenyl | 2-methylphenyl-O-CH₂CH₂-NMe₂ | 197–198ª | 3-{2-[2-(N,N-Dimethylamino)-ethyl]oxy-phenyl}-5-(3-methyl-phenyl)-1,2,4-oxadiazole |
| 124 | 4-methylphenyl | 2-methylphenyl-O-CH₂CH₂-NMe₂ | 189–191ª | 3-{2-[2-(N,N-Dimethylamino)-ethyl]oxy-phenyl}-5-(4-methyl-phenyl)-1,2,4-oxadiazole |
| 125 | phenyl | 2-methylphenyl-NH-CH₂CH₂-NMe₂ | 194–195ª | 3-{2-N-[2-(N',N'-Dimethylamino)-ethyl]aminophenyl}-5-phenyl-1,2,4-oxadiazole |
| 126 | 3-chlorophenyl | 2-methylphenyl-O-CH₂CH₂-NMe₂ | 195–196ª | 3-{2-[2-(N,N-Dimethylamino)-ethyl]oxy-phenyl}-5-(3-chloro-phenyl)-1,2,4-oxadiazole |
| 127 | 2-chlorophenyl(Me) | 2-methylphenyl-O-CH₂CH₂-NMe₂ | 156–157ª | 3-{2-[2-(N,N-Dimethylamino)-ethyl]oxy-phenyl}-5-(2-chloro-phenyl)-1,2,4-oxadiazole |
| 128 | 4-chlorophenyl | 2-methylphenyl-O-CH₂CH₂-NMe₂ | 209–210ª | 3-{2-[2-(N,N-Dimethylamino)-ethyl)oxy-phenyl}-5-(4-chloro-phenyl)-1,2,4-oxadiazole |
| 129 | phenyl | 2-methylphenyl-O-CH₂CH₂-morpholino | 166–167ª | 3-[2-(2-N-Morpholinoethyl)oxy-phenyl]-5-(3-methyl-phenyl)-1,2,4-oxadiazole |

TABLE 2-continued

Oxadiazoles of general formula (Ib)

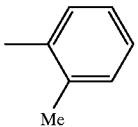

(Ib)

| Example | R¹ | Z | m.p. [° C.] | chemical name |
|---|---|---|---|---|
| 130 | 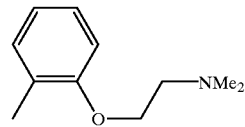 | 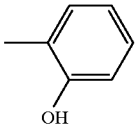 | 189–190[a] | 3-{2-[2-(N,N-Dimethylamino)-ethyl]oxy-phenyl}-5-(2-methyl-phenyl)-1,2,4-oxadiazole |
| 131 | 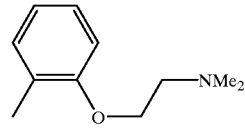 | 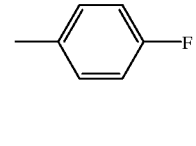 | 167–168[a] | 3-{2-[2-(N,N-Dimethylamino)-ethyl]oxy-phenyl}-5-(2-hydroxy-phenyl)-1,2,4-oxadiazole |
| 132 | 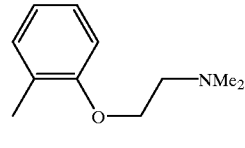 | 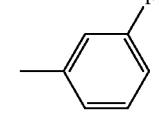 | 217–218[a] | 3-{2-[2-(N,N-Dimethylamino)-ethyl]oxy-phenyl}-5-(4-fluoro-phenyl)-1,2,4-oxadiazole |
| 133 | 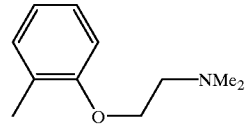 | 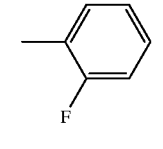 | 174–175[a] | 3-{2-[2-(N,N-Dimethylamino)-ethyl]oxy-phenyl}-5-(3-fluoro-phenyl)-1,2,4-oxadiazole |
| 134 | 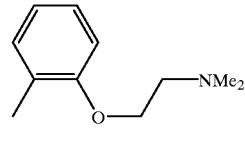 | 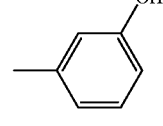 | 196–197[a] | 3-{2-[2-(N,N-Dimethylamino)-ethyl]oxy-phenyl}-5-(2-fluoro-phenyl)-1,2,4-oxadiazole |
| 135 | 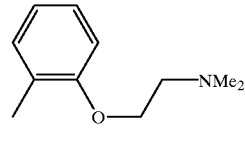 | 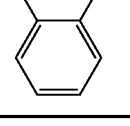 | 188–189[a] | 3-{2-[2-(N,N-Dimethylamino)-ethyl]oxy-phenyl}-5-(3-hydroxy-phenyl)-1,2,4-oxadiazole |
| 136 | 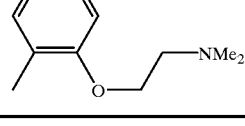 | | 144–145[a] | 3-{2-[2-(N,N-Dimethylamino)-ethyl]oxy-phenyl}-5-(2-methoxy-phenyl)-1,2,4-oxadiazole |

[a]hydrochloride

Surprisingly, it has been found that the compounds according to the invention have an affinity for all kinds of receptors and that they have a neuroprotective activity.

Tests in vitro and in vivo have shown that the cell damage and loss of function occurring in the brain as a result of hypoglycaemia, hypoxia, anoxia, global and focal ischaemia, skull and brain damage, brain swelling and cerebral pressure are partly due to an increased synaptic activity and hence increased release of transmitters. In addition to glutamate, histamine and serotonin are particularly important as neurotransmitters. Moreover, the concentrations of calcium and sodium ions, in particular, are changed.

It is known that after the systemic administration of glutamate, neurons in the brains of mice are destroyed (S. M. Rothman and T. W. Olney, Trends in Neurosciences 10 (1987) 299). This finding leads one to conclude, inter alia, that glutamate plays a part in neurodegenerative disorders (R. Schwarcz and B. Meldrum, The Lancet 11 (1985) 140). In addition, substances such as quisqualic acid, cainic acid, ibotenic acid, glutaminic acid, N-methyl-D-aspartic acid (NMDA) and α-amino-3-hydroxy-5-methyl-4-isooxazole-propionic acid (AMPA) are known as exogenous and endogenous neurotoxins. Brain lesions which may be induced with such substances are comparable with those which occur in connection with epilepsy and other neurodegenerative disorders such as Huntington's disease and Alzheimer's disease. Substances and ions which inhibit the activity of the glutamate receptors and the ion channel connected to this receptor—such as, for example, competitive and non-competitive antagonists of excitatory amino acids—protect brain cells from hypoxic and ischaemic damage. These findings show that the glutamate receptors play an important part in mediating ischaemic damage.

The activity on the AMPA receptor was demonstrated by means of electrophysiology on neuronal cells (using the Patch-Clamp-Method) (M. L. Mayer, L. Vyklicky and G. L. Westbrook, J. Physiol. 415 (1989) 329–350).

The tests were carried out at a test concentration of 100 $\mu$M.

TABLE 3

Inhibiting the cainate-induced signal at the AMPA receptor

| Example | AMPA Inh. [%] |
|---------|---------------|
| 21 | 98 |
| 17 | 97 |
| 34 | 97 |
| 8 | 97 |
| 3 | 96 |
| 13 | 96 |
| 14 | 96 |
| 24 | 96 |
| 22 | 94 |
| 23 | 93 |
| 37 | 93 |
| 27 | 91 |
| 20 | 90 |
| 28 | 87 |
| 33 | 87 |
| 2 | 86 |
| 12 | 85 |
| 19 | 86 |
| 48 | 85 |
| 5 | 84 |
| 55 | 81 |
| 68 | 81 |
| 18 | 80 |
| 42 | 79 |
| 43 | 77 |
| 4 | 71 |
| 64 | 65 |
| 45 | 64 |
| 44 | 62 |
| 47 | 59 |
| 59 | 54 |
| 57 | 51 |
| 40 | 37 |
| 67 | 28 |
| 31 | 23 |

The affinity for the "Na$^+$channel site 2"-binding site was demonstrated as described by G. B. Brown (J. Neurosci. 6 (1986) 2064). The tests were typically carried out at a test concentration of 10 $\mu$M. The inhibitory values are shown in Table 4.

TABLE 4

Inhibition on the Na-channel ([$^3$H]-BTX)

| Example | Na$^+$-channel Inh. [%] |
|---------|-------------------------|
| 14 | 100 |
| 20 | 100 |
| 21 | 100 |
| 68 | 100 |
| 23 | 99 |
| 64 | 99 |

TABLE 4-continued

Inhibition on the Na-channel ([$^3$H]-BTX)

| Example | Na$^+$-channel Inh. [%] |
|---------|-------------------------|
| 13 | 95 |
| 22 | 94 |
| 37 | 93 |
| 67 | 92 |
| 3 | 91 |
| 28 | 91 |
| 12 | 90 |
| 24 | 89 |
| 42 | 89 |
| 44 | 89 |
| 34 | 88 |
| 40 | 88 |
| 8 | 87 |
| 2 | 86 |
| 18 | 85 |
| 48 | 85 |
| 33 | 84 |
| 19 | 83 |
| 31 | 82 |
| 17 | 80 |
| 45 | 79 |
| 4 | 79 |
| 27 | 79 |
| 5 | 78 |
| 47 | 74 |
| 43 | 72 |
| 59 | 70 |
| 54 | 62 |
| 57 | 54 |

Cell damage caused by hypoglycaemia, hypoxia, anoxia and ischaemia, as a result of a lack of supply, lead to a reduced supply of energy carriers such as glucose in the neurons.

The effects of histamine receptor antagonists on hypoxia- and hypoglycaemia-induced damage on the uptake of 2-deoxyglucose was investigated in preparations of slices of hippocampus taken from the rat (S. Shibata and S. Watanabe, Neuroscience Letters 151 (1993) 138). The addition of histamine leads to a worsening of the ischaemia-induced reduction in the uptake of 2-deoxyglucose. It has been shown that histamine H1 receptor antagonists improve the ischaemia-induced reduction in the uptake of 2-deoxyglucose, whereas histamine H2 receptor antagonists have no effect on this. The protective effect of histamine H1 receptor antagonists can be removed using histamine. This investigation makes it clear that histamine receptors play an important part in ischaemia-induced reduction in the glucose metabolism.

Excessive neuronal activity, in conjunction with a massive increase in neurotransmitters, may lead to neuronal degeneration in animal models having transient cerebral ischaemia (H. Benveniste, H. Drejer, A. Schousboe, N. H. Diemer, J. Neurochem. 43 (1984) 1369). Neuronal activity can be inhibited by substances which bind to neurotransmitter receptors, such as, for example, 5-hydroxytryptamine (R. Andrade, R. A. Nicoll, Soc. Neurosci. Abstr. 11 (1985) 297). It was also shown that the administration of 5-hydroxytryptamine agonists in animal models with occlusion of the central cerebral artery resulted in a reduction in the volume of infarct (J. H. M. Prehn, C. Backhauβ, C. Karkoutly, J. Nuglisch, B. Peruche, C. Rossberg, J. Krieglstein, Eur. J. Pharmacol. 203 (1991) 213).

As a test system for demonstrating affinity for the following receptors, receptor binding studies were carried out as described in the following references: Histamine H1 (S.

Dini et al. Agents and Actions 33 (1991) 181); 5-hydroxytryptamine 1A (M. D. Hall et al., J. Neurochem. 44 (1985) 1685); 5-hydroxytryptamine 2A (J. E. Leysen et al., Mol. Pharmacol. 21 (1982) 301); The tests were typically carried out at a test concentration of 10 $\mu$M. Table 5 summarises the inhibitory values on the above receptors:

TABLE 5a

| Example | H1 Inh. [%] |
|---|---|
| 2 | 99 |
| 40 | 99 |
| 3 | 98 |
| 45 | 98 |
| 34 | 96 |
| 19 | 95 |
| 54 | 95 |
| 18 | 94 |
| 31 | 94 |
| 8 | 94 |
| 42 | 94 |
| 37 | 93 |
| 28 | 92 |
| 13 | 91 |
| 27 | 90 |
| 57 | 90 |
| 67 | 90 |
| 64 | 88 |
| 12 | 87 |
| 14 | 87 |
| 33 | 87 |
| 43 | 86 |
| 59 | 84 |
| 47 | 82 |
| 17 | 78 |
| 48 | 78 |
| 21 | 75 |
| 5 | 74 |
| 44 | 74 |
| 68 | 74 |
| 22 | 64 |
| 23 | 63 |
| 4 | 44 |
| 24 | 27 |
| 20 | 19 |

TABLE 5b

| Example | HT1A Inh. [%] |
|---|---|
| 8 | 100 |
| 47 | 98 |
| 27 | 97 |
| 33 | 97 |
| 19 | 96 |
| 34 | 95 |
| 37 | 94 |
| 31 | 93 |
| 64 | 93 |
| 2 | 91 |
| 13 | 91 |
| 17 | 91 |
| 24 | 91 |
| 45 | 91 |
| 18 | 90 |
| 40 | 88 |
| 23 | 87 |
| 54 | 85 |
| 68 | 84 |
| 3 | 79 |
| 22 | 77 |
| 42 | 77 |
| 28 | 75 |
| 57 | 72 |
| 43 | 69 |

TABLE 5b-continued

| Example | HT1A Inh. [%] |
|---|---|
| 44 | 65 |
| 5 | 63 |
| 12 | 56 |
| 48 | 54 |
| 4 | 50 |
| 67 | 49 |
| 21 | 48 |
| 59 | 46 |
| 20 | 43 |
| 14 | 28 |

TABLE 5c

| Example | HT2A Inh. [%] |
|---|---|
| 13 | 100 |
| 17 | 99 |
| 67 | 99 |
| 18 | 97 |
| 40 | 97 |
| 14 | 96 |
| 33 | 96 |
| 34 | 96 |
| 47 | 96 |
| 3 | 95 |
| 8 | 95 |
| 45 | 95 |
| 12 | 94 |
| 27 | 94 |
| 54 | 94 |
| 4 | 93 |
| 23 | 93 |
| 44 | 93 |
| 59 | 93 |
| 28 | 92 |
| 48 | 92 |
| 64 | 92 |
| 2 | 91 |
| 31 | 91 |
| 21 | 90 |
| 42 | 90 |
| 22 | 88 |
| 68 | 87 |
| 19 | 84 |
| 5 | 81 |
| 20 | 79 |
| 37 | 78 |
| 57 | 77 |
| 24 | 58 |
| 43 | 58 |

According to H. Takahashi et al. (Stroke 26 (1995) 1676) Sigma receptors are involved in the mechanism of acute damage after transient focal ischaemia. Takahashi et al. were able, for example, to demonstrate a reduction in the volume of infarct when investigating a potent ligand of the Sigma receptor in the model of transient focal ischaemia.

As a test system for demonstrating the affinity of the compounds according to the invention for the Sigma receptor, receptor binding studies were carried out in dance with E. W. Karbon, K. Naper, M. J. Pontecorvo, Eur. J. Pharmacol. 193 (1991) 21. The tests were typically carried out at a test concentration of 10 $\mu$M. The inhibitory values are shown in the following Table.

TABLE 6

| Example | Sigma Inh. [%] | Example | Sigma Inh. [%] |
|---|---|---|---|
| 14 | 93 | 64 | 76 |
| 44 | 93 | 34 | 75 |
| 5 | 90 | 19 | 74 |
| 45 | 85 | 48 | 74 |
| 20 | 84 | 12 | 68 |
| 27 | 84 | 54 | 68 |
| 28 | 84 | 17 | 65 |
| 13 | 83 | 2 | 62 |
| 37 | 82 | 3 | 62 |
| 59 | 82 | 8 | 59 |
| 18 | 80 | 42 | 57 |
| 23 | 79 | 47 | 56 |
| 68 | 79 | 67 | 54 |
| 22 | 78 | 24 | 52 |
| 31 | 77 | 57 | 49 |
| 33 | 77 | 4 | 41 |
| 21 | 76 | 43 | 0 |
| 40 | 76 | | |

The neuroprotective activity in vivo was demonstrated in a stroke model in the rat. A permanent focal cerebral ischaemia was induced by surgical occlusion of the arteria cerbri media (MCAO) (based on A. Tamura, D. I. Graham, J. McCulloch and G. M. Teasdale, J. Cereb. Blood Flow Metab. 1 (1981) 53–60). With 5-{2-[2-(N,N-dimethylamino)ethyl]oxy-phenyl}-3-phenyl-1,2,4-oxadiazole (Example 2) it was possible to reduce the volume of the lesion significantly.

The results described above show that the oxadiazole derivates of general formula I can be used in neurodegenerative disorders and cerebral ischaemia of various origins. These include, for example: epilepsy, hypoglycaemia, hypoxia, anoxia, brain trauma, brain oedema, amyotropic lateral sclerosis, Huntington's disease, Alzheimer's disease, hypotonia, cardiac infarct, cerebral pressure (increased intracranial pressure), ischaemic and haemorrhagic stroke, global cerebral ischaemia during heart stoppage, diabetic polyneuropathy, tinnitus, perinatl asphyxia, schizophrenia, depression and Parkinson's disease.

The compounds of general formula (I) may be used on their own or in conjunction with other active substances according to the invention, optionally also in conjunction with other pharmacologically active substances. Suitable forms for administration include tablets, capsules, suppositories, solutions—particularly solutions for injection (s.c., i.v., i.m.) and liquids for infusion, emulsions or dispersible powders. The proportion of the pharmaceutically active compound or compounds should be in the range from 0.1 to 90% by weight, preferably 0.5 to 50% by weight of the total composition, i.e. in quantities sufficient to achieve the dosage range specified below. Suitable tablets may be obtained, for example, by mixing the active substance or substances with known excipients, e.g. inert diluents such calcium carbonate, calcium phosphate or lactose, disintegrants such as corn starch or alginic acid, binders such as starch or gelatine, lubricants such as magnesium stearate or talc, and/or agents for obtaining delayed release such as carboxymethylcellulose, cellulose acetate phthalate or polyvinylacetate. The tablets may also consist of several layers.

Accordingly, coated tablets may be produced by covering cores made in the same way as the tablets with agents conventionally used for tablet coatings, e.g. collidone or shellac, gum arabic, talc, titanium dioxide or sugar. In order to achieve delayed release or prevent intolerance, the core may consist of several layers. Similarly, the tablet coating may be made up of a number of layers to achieve delayed release, and the excipients used for the tablets above may be used here.

Syrups containing the active substances or combinations of active substances according to the invention may additionally contain a sweetener such as saccharin, cyclamate, glycerol or sugar and a flavour enhancer, e.g. a flavouring such as vanillin or orange extract. They may also contain suspension adjuvants or thickeners such as sodium carboxymethylcellulose, wetting agents, e.g. condensation products of fatty alcohols with ethylene oxide, or protective substances such as p-hydroxybenzoates.

Solutions for injection and infusion are prepared in the usual way, e.g. with the addition of isotonic agents, preservatives such as p-hydroxybenzoates or stabilisers such as alkali metal salts of ethylene diamine tetraacetic acid, optionally using emulsifiers and/or dispersants, whilst if water is used as a diluent, organic solvents may optionally be used as solubilizers or solvating agents, and these solutions are then packed into injection vials or ampoules or infusion bottles.

Capsules containing one or more active substances or combinations of active substances may be prepared, for example, by mixing the active substances with inert carriers such as lactose or sorbitol and encapsulating them in gelatine capsules. Suitable suppositories may be prepared, for example, by mixing with carriers provided for this purpose, such as neutral fats or polyethyleneglycol or derivatives thereof.

Examples of excipients include water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as natural mineral powders (e.g. kaolines, clays, talc and chalk) synthetic mineral powders (e.g. highly dispersed silica and silicates), sugar (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium laurylsulphate).

The preparations are administered in the usual way, preferably by parenteral route, most particularly by infusion, intravenously. In the event of oral administration, in addition to the above-mentioned carriers, the tablets may, of course, also contain additives such as sodium citrate, calcium carbonate and dicalcium phosphate, together with various additives such as starch, preferably potato starch, gelatine and the like. In addition, lubricants such as magnesium stearate, sodium laurylsulphate and talc may be used for producing the tablets. In the case of aqueous suspensions, the active substances may be combined with various flavour enhancers or colourings, in addition to the above-mentioned excipients.

For parenteral use, solutions of the active substances may be administered, using suitable liquid carriers. The dosage for intravenous use is from 1–1,000 mg per hour, preferably between 5–500 mg per hour.

However, it may be necessary to deviate from these quantities, depending on the body weight and the route of administration, individual response to the drug, the type of formulation used and the time or interval at which it is administered. Thus, in some cases, a quantity less than the minimum may be sufficient, whereas in other cases the upper limit will have to be exceeded. When larger amounts are administered, it may be advisable to divide them into a number of single doses spread over the day.

Moreover, the compounds of general Formula I or the acid addition salts thereof may also be combined with other types of active substance.

The Examples which follow illustrate the present invention without restricting its scope:

Examples of Pharmaceutical Formulations

| A) Tablets | per tablet |
|---|---|
| Active substance | 100 mg |
| Lactose | 140 mg |
| Corn starch | 240 mg |
| Polyvinylpyrrolidone | 15 mg |
| Magnesium stearate | 5 mg |
| | 500 mg |

The finely ground active substance, lactose and some of the corn starch are mixed together. The mixture is screened, then moistened with a solution of polyvinylpyrrolidone in water, kneaded, granulated whilst moist and dried. The granules, the remaining corn starch and the magnesium stearate are screened and mixed together. The mixture is compressed to form tablets of suitable shape and size.

| B) Tablets | per tablet |
|---|---|
| Active substance | 80 mg |
| Lactose | 55 mg |
| Corn starch | 190 mg |
| Microcrystalline cellulose | 35 mg |
| Polyvinylpyrrolidone | 15 mg |
| Sodium carboxymethyl starch | 23 mg |
| Magnesium stearate | 2 mg |
| | 400 mg |

The finely ground active substance, some of the corn starch, lactose, microcrystalline cellulose and polyvinylpyrrolidone are mixed together, the mixture screened and processed with the remaining corn starch and water to form a granulate which is dried and screened. The sodium carboxymethyl starch and the magnesium stearate are added thereto, the ingredients are mixed and the mixture is compressed to form tablets of a suitable size.

| C) Ampoule solution | |
|---|---|
| Active substance | 50 mg |
| Sodium chloride | 50 mg |
| Water for injections | 5 ml |

The active substance is dissolved in water at its own pH or possibly at pH 5.5 to 6.5 and sodium chloride is added to make the solution isotonic. The resulting solution is filtered to remove pyrogens and the filtrate is transferred under aseptic conditions into ampoules which are then sterilised and sealed by fusion. The ampoules contain 5 mg, 25 mg and 50 mg of active substance.

What is claimed is:
1. A compound of the formula I

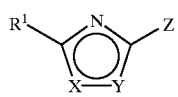

wherein:
X and Y denote oxygen or nitrogen, wherein X and Y cannot both simultaneously be oxygen or nitrogen,
Z denotes a group of formula

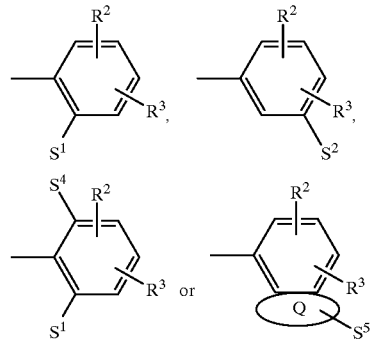

wherein
$S^1$ denotes a group of formula

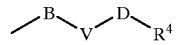

wherein V represents oxygen, sulphur or $NR^7$ and B and D, which are identical or different, denote a $C_{1-4}$-alkylene, $C_{2-4}$-alkenylene or $C_{2-4}$-alkynylene bridge, which is optionally substituted by =O, —$OR^7$, phenyl or halogen (which is fluorine, chlorine or bromine),
$S^1$ denotes a group of formula

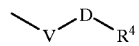

wherein V and D are as hereinbefore defined,
$S^1$ denotes a group of formula

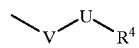

wherein V is as hereinbefore defined and U represents a $C_{3-6}$-cycloalkyl or phenyl group which is optionally substituted by $C_{1-4}$-alkyl, —OR7, $C_{6-10}$-aryl or halogen (which is fluorine, chlorine or bromine),
$S^1$ denotes a group of formula

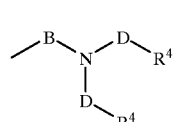

wherein B and D are as hereinbefore defined and the two groups D and the two groups $R^4$ are identical or different, $S^1$ denotes a group of formula

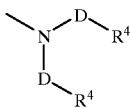

wherein D is as hereinbefore defined and the two groups D and the two groups $R^4$ are identical or different, $S^1$ denotes a group of formula

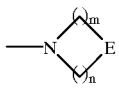

wherein E denotes oxygen, sulphur or $NR^7$ (with n,m=1,2 or 3 and n+m>2), and the group is optionally substituted by halogen (which is fluorine, chlorine or bromine), =O, $OR^7$, or one or more $C_1$–C4-alkyl groups;

$S^1$ denotes a group of formula

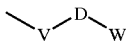

wherein V and D are as hereinbefore defined and W is a group of the formula

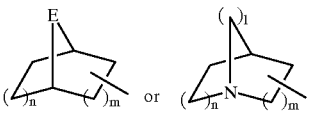

optionally substituted by halogen, =O, —$OR^7$, —$OCOR^7$, $C_{1-4}$-alkyl, $C_{2-6}$-alkenyl or $C_{2-6}$-alkynyl, wherein E denotes oxygen or N $R^7$ and n, m and l are each 0, 1 or 2, or W is a C-linked 5- or 6-membered heterocyclic group which contains one or more heteroatoms from the group consisting of nitrogen, oxygen and sulphur, and is optionally substituted by benzyl or $C_{1-4}$-alkyl;

$S^1$ denotes a group of formula

wherein V and W are as hereinbefore defined;

$S^2$ denotes a group of formula

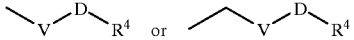

wherein V and D are as hereinbefore defined, $S^4$ denotes a group of formula

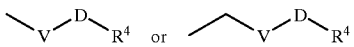

wherein V and D are as hereinbefore defined,

Q denotes a fused-on, mono- or polyunsaturated 5- or 6-membered heterocyclic ring which optionally contains one or more heteroatoms from the group consisting of oxygen, nitrogen and sulphur, and is optionally substituted by $OR^7$, $NR^5R^6$, halogen, CN, nitro, $CF_3$, $COOR^7$, $C_{1-4}$-alkyl, $C_{2-4}$-alkenyl or $C_{2-4}$-alkynyl;

$S^5$ denotes a group of formula

wherein D is as hereinbefore defined;

$R^1$ denotes benzyl or phenyl, wherein the phenyl ring is optionally mono- or polysubstituted by one or more of the following groups: fluorine, chlorine or bromine, $C_1$–$C_4$-alkyl, —$CF_3$, —$CR^7$=$NOR^7$ (wherein the groups $R^7$ are identical or different), —$NMe_2$, $Net_2$, —$NO_2$ or —$OR^7$, $R^1$ denotes phenyl, which is substituted by a group of formula

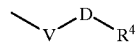

with the proviso that V is oxygen or $NR^7$ and D represents a $C_{1-4}$-alkyl bridge, $R^1$ denotes a C- or N-linked 5 or 6-membered heterocycle which contains one or more heteroatoms from the group consisting of nitrogen, oxygen and sulphur, and is optionally mono- or polysubstituted by benzyl, methyl, fluorine, chlorine, bromine or hydroxy, $R^1$ denotes cyclopropyl, cyclopentyl or cyclohexyl, which is optionally substituted by =O or —$OR^7$, $R^1$ denotes norbornane, norbornene, dicyclopropylmethyl, adamantane or noradamantane, which are optionally substituted by methyl, $R^1$ denotes a group of formula

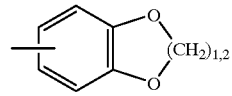

$R^1$ denotes —CH=CH-phenyl, wherein the phenyl ring is optionally substituted by methoxy or hydroxy, $R^2$ denotes hydrogen, fluorine, chlorine or bromine, $C_{1-4}$-alkyloxy, $C_{1-4}$-alkyl or hydroxy, $R^3$ denotes hydrogen;

$R^4$ denotes hydroxy, CN or —$NR^5R^6$;

$R^4$ denotes an N-oxide of formula

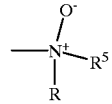

$R^5$ denotes hydrogen, $C_{1-3}$-alkyl, benzyl or phenyl;

$R^6$ denotes hydrogen, $C_{1-3}$-alkyl, benzyl or phenyl; or $R^5$ and $R^6$ together with the nitrogen atom form a saturated or unsaturated 5- or 6-membered ring, which optionally contains, as further heteroatoms, nitrogen or oxygen, wherein the heterocycle is optionally mono- or polysubstituted by methyl;

$R^7$ denotes hydrogen, $C_1$–$C_4$-alkyl, a benzyl or phenyl group, wherein the phenyl ring is optionally mono- or polysubstituted by OH or $OCH_3$;

or a pharmacologically acceptable acid addition salt thereof.

2. A compound of the formula (I) according to claim 1 wherein:

X and Y denote oxygen or nitrogen, where X and Y do not both simultaneously represent oxygen or nitrogen, Z denotes a group of formula

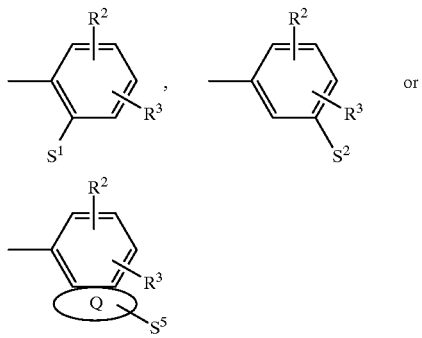

wherein
S¹ denotes a group of formula

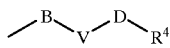

wherein V denotes oxygen, sulphur or NR⁷, B is —CH₂ and D is one of the groups —CH₂, —CH₂—CH₂—, —CH₂—CH₂—CH₂—, —CH₂—C(CH₃)H—, —CH₂—CO or CH₂—CH₂—CO;

S¹ denotes a group of formula

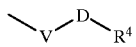

wherein V and D are as hereinbefore defined,

S¹ denotes piperazin-1-yl, 4-methyl-piperazin-1-yl or 4-benzyl-piperazin-1-yl;

S¹ denotes a group of formula

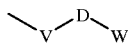

wherein V and D are as hereinbefore defined and W is a group of the formula

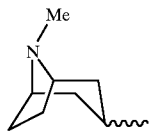

optionally substituted by C₁₋₄-alkyl,
or W is a C-linked 5-or 6-membered nitrogen heterocycle which is optionally substituted by benzyl or C₁₋₄-alkyl;

S¹ denotes a group of formula

wherein V and W are as hereinbefore defined;
S² denotes a group of formula

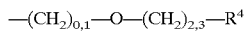

Q denotes a fused-on, mono- or polyunsaturated 5- or 6-membered ring which optionally contains a heteroatom selected from the group consisting of oxygen, nitrogen and sulphur;

S5 denotes a group of the formula

wherein D is as hereinbefore defined;

R¹ denotes cyclopropyl, cyclopentyl, benzyl or phenyl, wherein the phenyl ring is optionally mono- or polysubstituted by one or more of the groups fluorine, chlorine, bromine, C₁₋₄-alkyl, —CF₃, —CMe=NOH, —NO₂ or —OR⁷, R¹ denotes phenyl which is substituted by a group of formula

R¹ denotes furan, thiophene, pyridine or pyrrole, which is optionally mono- or polysubstituted by methyl, R¹ denotes norbornane, norbornene, adamantane or noradamantane, R¹ denotes —CH=CH-phenyl, wherein the phenyl ring is optionally substituted by hydroxy;

R² denotes hydrogen, fluorine, chlorine, bromine, C₁₋₄-alkyloxy, C₁₋₄-alkyl or hydroxy;

R³ denotes hydrogen;

R⁴ denotes N-morpholinyl, N-pyrrolidinyl, N-piperidinyl, N-piperazinyl, 4-methyl-piperazin-1-yl or 4-benzyl-piperazin-1-yl;

R⁴ denotes CN, NR⁵R⁶ or an N-oxide of formula

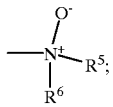

R⁵ denotes hydrogen, C₁₋₃-alkyl, benzyl or phenyl;
R⁶ denotes hydrogen, C₁₋₃-alkyl, benzyl or phenyl;
R⁷ denotes hydrogen, methyl, ethyl, propyl, isopropyl, butyl, tert.-butyl, a benzyl or phenyl group, wherein the phenyl ring is optionally mono- or polysubstituted by OH or OCH₃, or a pharmacologically acceptable acid addition salt thereof.

3. A compound of the formula (I) according to claim 1, wherein:

X and Y denote oxygen or nitrogen, where X and Y do not both simultaneously represent oxygen or nitrogen, Z denotes a group of formula

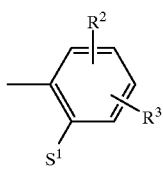

wherein
S¹ denotes a group of formula

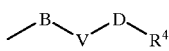

wherein V denotes oxygen, sulphur or NR⁷, B is —CH₂ and D is one of the groups —CH₂, —$CH_2$—$CH_2$—, —$CH_2$—$CH_2$—$CH_2$—, —$CH_2$—$C(CH_3)H$—, —$CH_2$—CO or $CH_2$—$CH_2$—CO;

$S^1$ denotes a group of formula

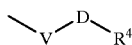

wherein V and D are as hereinbefore defined, $S^1$ denotes piperazin-1-yl, 4-methyl-piperazin-1-yl or 4-benzyl-piperazin-1-yl;

$S^1$ denotes a group of formula

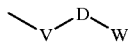

wherein V and D are as hereinbefore defined and W is a group of the formula

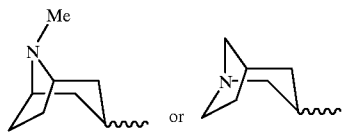

optionally substituted by $C_{1-4}$-alkyl, or W is a C-linked 5- or 6-membered nitrogen heterocycle which is optionally substituted by benzyl or $C_{1-4}$-alkyl;

$S^1$ denotes a group of formula

wherein V and W are as hereinbefore defined;

Q denotes a fused-on, mono- or polyunsaturated 5- or 6-membered heterocyclic ring which optionally contains a heteroatom selected from the group consisting of oxygen, nitrogen and sulphur;

$S^5$ denotes a group of the formula

wherein D is as hereinbefore defined;

$R^1$ denotes cyclopropyl, cyclopentyl or phenyl, wherein the phenyl ring is optionally mono- or polysubstituted by one or more of the groups fluorine, chlorine, bromine, $C_{1-4}$-alkyl, —$CF_3$, —CMe=NOH, —$NMe_2$, —$NO_2$ or —$OR^7$, $R^1$ denotes furan, thiophene, pyridine or pyrrole, which is optionally mono- or polysubstituted by methyl, $R^1$ denotes norbornane, norbornene, adamantane or noradamantane, $R^1$ denotes —CH=CH-phenyl, wherein the phenyl ring is optionally substituted by hydroxy;

$R^2$ denotes hydrogen, fluorine, chlorine, bromine, $C_{1-4}$-alkyloxy, $C_{1-4}$-alkyl or hydroxy;

$R^3$ denotes hydrogen;

$R^4$ denotes CN, $NR^5R^6$ or an N-oxide of formula

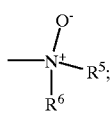

$R^4$ denotes N-morpholinyl, N-pyrrolidinyl, N-piperidinyl, N-piperazinyl, 4-methyl-piperazin-1-yl or 4-benzyl-piperazin-1-yl;

$R^5$ denotes hydrogen, $C_{1-3}$-alkyl, benzyl or phenyl;

$R^6$ denotes hydrogen, $C_{1-3}$-alkyl, benzyl or phenyl;

$R^7$ denotes hydrogen, methyl, ethyl, propyl, isopropyl, butyl, tert.-butyl, a benzyl or phenyl group, wherein the phenyl ring is optionally mono- or polysubstituted by OH or $OCH_3$, or a pharmacologically acceptable acid addition salt thereof.

4. A compound of the formula (I) according to claim 1, wherein:

X and Y denote oxygen or nitrogen, where X and Y do not both simultaneously represent oxygen or nitrogen, Z denotes a group of formula

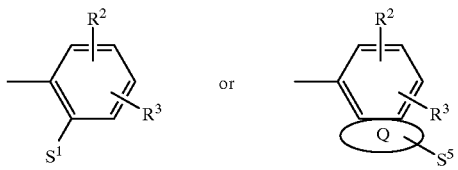

wherein $S^1$ denotes a group of formula

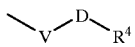

wherein V denotes oxygen, sulphur or $NR^7$ and D is one of the groups —$CH_2$, —$CH_2$—$CH_2$—, —$CH_2$—$CH_2$—$CH_2$—, —$CH_2$—$C(CH_3)H$—, —$CH_2$—CO or $CH_2$—$CH_2$—CO;

denotes piperazin-1-yl, 4-methyl-piperazin-1-yl or 4-benzyl-piperazin-1-yl;

$S^1$ denotes a group of formula

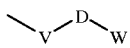

wherein V and D are as hereinbefore defined and W is a group of the formula

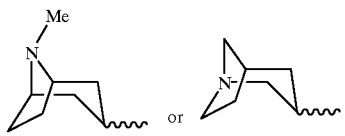

or W is a C-linked 5- or 6-membered nitrogen heterocycle which is optionally substituted by methyl;

$S^1$ denotes a group of formula

wherein V and W are as hereinbefore defined;

Q denotes a fused-on, mono- or polyunsaturated 5- or 6-membered heterocyclic ring contains a heteroatom selected from the group consisting of oxygen and nitrogen;

$S^5$ denotes a group of the formula

wherein D is as hereinbefore defined;

$R^1$ denotes phenyl which is optionally mono- or polysubstituted by one or more of the groups fluorine, chlorine, bromine, methyl, ethyl, n-propyl, isopropyl, n-butyl, tert. butyl, —$CF_3$ or —$OR^7$, $R^1$ denotes furan, thiophene or pyridine, which is optionally mono- or polysubstituted by methyl, $R^2$ denotes hydrogen, fluorine, chlorine, bromine, methyl, methyloxy or hydroxy;

$R^3$ denotes hydrogen;

$R^4$ denotes $NR^5R^6$ or an N-oxide of formula

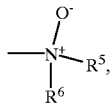

$R^4$ denotes N-morpholinyl, N-pyrrolidinyl, N-piperidinyl, N-piperazinyl, 4-methyl-piperazin-1-yl or 4-benzyl-piperazin-1-yl;

$R^5$ denotes hydrogen, methyl, ethyl, n-propyl, isopropyl, benzyl or phenyl;

$R^6$ denotes hydrogen, methyl, ethyl, n-propyl, isopropyl, benzyl or phenyl;

$R^7$ denotes hydrogen, methyl or ethyl, or a pharmacologically acceptable acid addition salt thereof.

5. A compound of the formula (I) according to claim 1, wherein

X and Y denote oxygen or nitrogen, but X and Y do not both simultaneously represent oxygen or nitrogen, Z denotes a group of formula

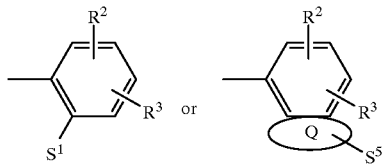

wherein $S^1$ denotes a group of formula

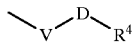

wherein V denotes oxygen and D is one of the groups —$CH_2$—, —$C_2$—$CH_2$—, —$CH_2$—$C(CH_3)H$— or $CH_2$—$CH_2$—CO;

$S^1$ denotes N-piperazinyl or 4-benzyl-piperazin-1-yl;

$S^1$ denotes a group of formula

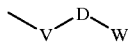

wherein V and D are as hereinbefore defined and W is a group of the formula

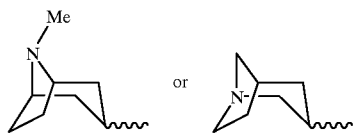

or W is a C-linked 5- or 6-membered nitrogen heterocycle which is optionally substituted by methyl;

$S^1$ denotes a group of formula

—V—W wherein V and W are as hereinbefore defined;

Q denotes a fused-on, mono- or polyunsaturated 5-membered heterocyclic ring which contains oxygen as heteroatom;

$S^5$ denotes a group of the formula

—D—$R^4$ wherein D is as hereinbefore defined;

$R^1$ denotes phenyl which is optionally mono- or polysubstituted by one or more of the groups fluorine, chlorine, bromine, methyl, —$CF_3$, hydroxy, methyloxy or ethyloxy, $R^1$ denotes furan, thiophene or pyridine;

$R^2$ denotes hydrogen, fluorine, chlorine or methyl;

$R^3$ denotes hydrogen;

$R^4$ denotes $NR^5R^6$, $R^4$ denotes N-morpholinyl, N-pyrrolidinyl, N-piperidinyl or 4-methyl-piperazin-1-yl;

$R^5$ denotes hydrogen, methyl, ethyl, n-propyl, isopropyl, benzyl or phenyl;

$R^6$ denotes hydrogen, methyl, ethyl, n-propyl, isopropyl, benzyl or phenyl;

or a pharmacologically acceptable acid addition salt thereof.

6. A compound of the formula (I) according to claim 1, wherein:

X and Y denote oxygen or nitrogen, but X and Y do not both simultaneously represent oxygen or nitrogen, Z denotes a group of formula

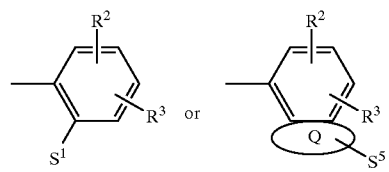

wherein $S^1$ denotes one of the groups —O—$CH_2$—$CH_2$—$R^4$, O—$CH_2$—$C(CH_3)H$—$R^4$, —O—$C(CH_3)H$—$CH_2$—$R^4$ or —$CH_2$—$CH_2$—CO—$R^4$;

$S^1$ denotes 4-benzyl-piperazin-1-yl;

$S^1$ denotes one of the groups

—O—$CH_2$—W or —O—W wherein W is a C-linked 5- or 6-membered nitrogen heterocycle which is optionally substituted by methyl;

Q denotes a fused-on, mono- or polyunsaturated 5-membered heterocyclic ring which contains oxygen as heteroatom;

$S^5$ denotes a group of the formula —$CH_2$—$R^4$;

$R^1$ denotes phenyl which is optionally mono- or polysubstituted by one or more of the groups fluorine, chlorine, bromine, methyl, —$CF_3$, hydroxy, methyloxy or ethyloxy, $R^1$ denotes thiophene;

$R^2$ denotes hydrogen, fluorine, chlorine or methyl;

$R^3$ denotes hydrogen;

$R^4$ denotes $NR^5R^6$, $R^4$ denotes N-pyrrolidinyl or N-piperidinyl;

$R^5$ denotes hydrogen, methyl, ethyl, isopropyl, benzyl or phenyl;

$R^6$ denotes hydrogen, methyl, ethyl, isopropyl, benzyl or phenyl;

or a pharmacologically acceptable acid addition salt thereof.

7. A pharmaceutical composition comprising a compound of the formula I in accordance with claim 1 and a pharmaceutically acceptable carrier.

8. A method for treating cerebral ischaemia which comprises administering to a host suffering from cerebral ischemia a therapeutically effective amount of a compound of the formula I in accordance with claim 1, 2, 3, 4, 5 or 6.

\* \* \* \* \*